United States Patent
Horne et al.

(10) Patent No.: US 9,416,156 B2
(45) Date of Patent: *Aug. 16, 2016

(54) METHOD OF MAKING BIOLOGICALLY ACTIVE ALPHA-BETA PEPTIDES

(71) Applicant: Wisconsin Alumni Research Foundation, Madison, WI (US)

(72) Inventors: William S. Horne, Pittsburgh, PA (US); Samuel H. Gellman, Madison, WI (US); Lisa M. Johnson, Marshall, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/150,125

(22) Filed: Jan. 8, 2014

(65) Prior Publication Data

US 2014/0315791 A1 Oct. 23, 2014

Related U.S. Application Data

(63) Continuation of application No. 12/578,993, filed on Oct. 14, 2009, now Pat. No. 8,642,536.

(60) Provisional application No. 61/106,205, filed on Oct. 17, 2008, provisional application No. 61/229,325, filed on Jul. 29, 2009.

(51) Int. Cl.
| | | |
|---|---|---|
| *A01N 37/18* | (2006.01) | |
| *A61K 38/00* | (2006.01) | |
| *A61P 31/18* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 1/00* | (2006.01) | |
| *C07K 7/02* | (2006.01) | |
| *C07K 14/00* | (2006.01) | |
| *C07K 14/005* | (2006.01) | |
| *C07K 14/47* | (2006.01) | |
| *C07K 1/107* | (2006.01) | |

(52) U.S. Cl.
CPC .............. *C07K 1/006* (2013.01); *C07K 1/107* (2013.01); *C07K 7/02* (2013.01); *C07K 14/00* (2013.01); *C07K 14/001* (2013.01); *C07K 14/005* (2013.01); *C07K 14/4702* (2013.01); *C12N 2740/16122* (2013.01)

(58) Field of Classification Search
USPC ....................................................... 530/333
See application file for complete search history.

(56) References Cited

U.S. PATENT DOCUMENTS

| | | |
|---|---|---|
| 4,810,777 A | 3/1989 | Zasloff |
| 4,980,359 A | 12/1990 | Hasspacher et al. |
| 5,075,318 A | 12/1991 | Haefliger |
| 5,116,816 A | 5/1992 | Dreyfuss et al. |
| 5,190,941 A | 3/1993 | Nozulak et al. |
| 5,665,772 A | 9/1997 | Cottens et al. |
| 6,060,585 A | 5/2000 | Gellman et al. |
| 6,221,844 B1 | 4/2001 | Stump et al. |
| 6,440,990 B1 | 8/2002 | Cottens et al. |
| 6,613,876 B1 | 9/2003 | Gellman et al. |
| 2003/0212250 A1 | 11/2003 | Seebach |
| 2007/0087404 A1 | 4/2007 | Stahl et al. |
| 2007/0123709 A1 | 5/2007 | Gellman et al. |
| 2007/0154882 A1 | 7/2007 | Compton et al. |
| 2008/0058548 A1 | 3/2008 | Chi et al. |
| 2008/0166388 A1 | 7/2008 | Palecek et al. |

FOREIGN PATENT DOCUMENTS

| | | |
|---|---|---|
| EP | 0189002 A2 | 7/1986 |
| EP | 0296122 A2 | 12/1988 |
| EP | 0296123 A2 | 12/1988 |
| EP | 0433239 A1 | 6/1991 |
| EP | 0483063 A1 | 4/1992 |
| EP | 0505322 A1 | 9/1992 |
| EP | 0534904 A1 | 3/1993 |
| EP | 0606044 A1 | 7/1994 |
| EP | 0618223 A2 | 10/1994 |
| EP | 0641787 A1 | 3/1995 |
| EP | 0664289 A2 | 7/1995 |
| GB | 2206115 A | 12/1988 |

(Continued)

OTHER PUBLICATIONS

Horne et al. "Helix Bundle Quaternary Structure from a/b-Peptide Foldamers" J. Am. Chem. Soc. 129:4178-4180. Published Mar. 16, 2007.*

(Continued)

*Primary Examiner* — Christina Bradley
*Assistant Examiner* — Zachary J Miknis
(74) *Attorney, Agent, or Firm* — Joseph T. Leone, Esq.; DeWitt Ross & Stevens S.C.

(57) ABSTRACT

Described is a method of fabricating biologically active, unnatural polypeptides. The method includes the steps of selecting a biologically active polypeptide or biologically active fragment thereof having an amino acid sequence comprising α-amino acid residues, and fabricating a synthetic polypeptide that has an amino acid sequence that corresponds to the sequence of the biologically active polypeptide, but wherein about 14% to about 50% of the α-amino acid residues found in the biologically active polypeptide or fragment of step (a) are replaced with β-amino acid residues, and the α-amino acid residues are distributed in a repeating pattern.

6 Claims, 17 Drawing Sheets

(56) References Cited

FOREIGN PATENT DOCUMENTS

Figure 2A:

| GB | 2213482 A | 8/1989 |
|---|---|---|
| GB | 2218102 B | 11/1989 |
| GB | 2239178 A | 6/1991 |
| GB | 2240476 A | 8/1991 |
| WO | WO 89/09786 A1 | 10/1989 |
| WO | WO 94/02510 A2 | 2/1994 |
| WO | WO 94/09010 A1 | 4/1994 |
| WO | WO 94/12493 A1 | 6/1994 |
| WO | WO 9420526 A1 | 9/1994 |
| WO | WO 0039165 A1 | 7/2000 |

OTHER PUBLICATIONS

Schmitt et al. "New Helical Foldamers: Heterogenous Backbones with 1:2 and 2:1 a:b-Amino Acid Residue Patterns" J. Am. Chem. Soc. 128:4538-4539. Published Mar. 22, 2006.*
Adams et al., (2007), The Bcl-2 apoptotic switch in cancer development and therapy, *Oncogene*, 26:1324-1337.
Barlos et al., (1989) *Tetrahedron Lett.*, 30, 3943.
Berge, S.M. et al., (1977) Pharmaceutical Salts, *J. Pharm. Sci.*, 66:1-19.
Burkhard et al., (2000), Design of a minimal protein oligomerization domain by a structural approach, *Prot. Sci.*, 9:2294-2301.
Castano et al., (2008) EPH receptors in cancer, *Histol. Histopathol.*, 23(8):1011-1023.
Chan et al., (1997) Core Structure of gp41 from the HIV Envelope Glycoprotein, *Cell* 89:263-273.
Chan et al., (1998) Evidence that a prominent cavity in the coiled coil of HIV type 1 p. 41 is an attractive drug target, *Proc. Natl. Acad. Sci. USA* 95:15613-7.
Chen et al. (2005) *Mol. Cell*, 17:393-403.
Connor et al., (1997), Change in coreceptor use correrlates with disease progression in HIV-1infected individuals, *J. Exp. Med.*, 185(4):621-628.
Cook et al., (1993) Platelet Aggregation and Fibrinogen Binding in Human, Rhesus Monkey, Guinea-Pig, Hamster and Rat Blood: Activation by ADP and a Thrombin Receptor Peptide and Inhibition by Glycoprotein IIb / IIIa Antagonists, *Thrombosis and Haemostasis* 70(3):531-539.
Cook et al., (1993b), The Effects of Two Synthetic Glycoprotein IIb / IIIa Antagonists, Ro 43-8857 and L-700,462, on Platelet Aggregation and Bleeding in Guinea-Pigs and Dogs: Evidence that Ro 43-8857 Is Orally Active, *Thrombosis and Haemostasis* 70(5):838-847.
Dado et al., (1994) Intramolecular Hydrogen Bonding in Derivatives of (β-Alanine and γ-Amino Butyric Acid: Model Studies for the Folding of Unnatural Polypeptide Backbones, *J. Amer. Chem. Soc.* 116:1054-1062.
Deng et al., (2007), Protein design of a bacterially expressed HIV-1 gp41 fusion inhibitor, *Biochemistry*, 46:(14):4360-4369.
Dwyer et al., (2007), Design of helical, oligomeric HIV-1 fusion inhibitor peptides with potent activity against enfuvirtide-resistant virus, *PNAS*, vol. 104, No. 31, pp. 12722-12777.
Ellman, (1996 ) Design, Synthesis, and Evaluation of Small-Molecule Libraries, *Acc. Chem. Res.* 29:132-143.
Emsley et al., (2004) Coot: Model-building tools for molecular graphics, *Acta Crystallogr, Sect D*, 60:2126-2132.
Erdélyi et al., (2002), Rapid Microwave-Assisted Solid Phase Peptide Synthesis, *Synthesis*, 11:1592-1596.
Este et al., (2007), HIV entry inhibitors, *Lancet*, 370:81-88.
Fischer et al., (2003), Extending the Applicability of Carboxyfluorescein in Solid-Phase Synthesis, *Bioconjugate Chem.*, 14:653-660.
Frey et al., (2006), Small molecules that bind the inner core of gp41 and inhibit HIV envelope-mediated fusion, *Proc. Natl. Acad. Sci. U.S.A.*, 103:13938-13943.
Gill et al., (1989), Calculation of Protein Extinction Coefficients from Amino Acid Sequence Data, *Anal. Biochem.*, 182:319-326.

*Handbook of Pharmaceutical Salts*, P.H. Stahl and C.G. Wemuch, Eds., © 2002, Verlag Helvitica Chemica Acta (Zurich, Switzerland).
Hancock et al., *Anal. Biochem.*, 1976, 71, 260.
Horne et al., (2007), Helix Bundle Quaternary Structure from α/β-Peptide Foldamers, *J. Am. Chem. Soc.*, 129:4178-4180.
Horne et al., (2008), Sequence-based design of a α/β-peptide foldamers that mimic BH3 domains, *Agnew. Chem. Int. Ed.*, 47(15):2853-2856.
Horne, W. Seth, et al., (2008), "Foldamers with Heterogeneous Backbones," *Accounts of Chemical Research*, pp. 1399-1408, vol. 41, No. 10.
Horne, W. Seth, et al., (2008), "Interplay Among Side Chain Sequence, Backbone Composition, and Residue Rigidification in Polypeptide Folding and Assembly," *PNAS*, pp. 9151-9156, vol. 105, No. 27.
Horne, W. Seth, et al., (2009), "Structural and Biological Mimicry of Protein Surface Recognition by α/β-Peptide Foldamers," *PNAS*, pp. 14751-14756, vol. 106, No. 35.
Huck and Gellman, (2005). Synthesis of 2,2-Disubstituted Pyrrolidine-4- carboxylic Acid Derivatives and Their Incorporation into Beta-Peptide Oligomers, *J. Org. Chem.*, 70(9), 3353-62.
Lam et al., (1997) The "One-Bead-One-Compound" Combinatorial Library Method, *Chem. Rev.* 97:411-448.
Lamb et al., (2007), Structural basis of viral invasion: lessons from paramyxovirus E, *Structural Biology*, 17:427-436.
Lamzin et al. (1993), Automated refinement of protein models, *Acta Crystallogr*, Sect D, 49:129-147.
Lee et al., (2001), An Efficient Route to Either Enantiomer of Orthogonally Protected trans-3-Aminopyrrolidine-4-carboxylic Acid, *J. Org. Chem.*, 66:3597-3599.
Leplae et al., (2001), An Efficient Route to Either Enantiomer of trans-2-Aminocyclopentanecarboxylic Acid, *J. Org. Chem.* 66:5629-5632.
Louwagie et al., (1995), Genetic diversity of the envelope glycoprotein from human immunodeficiency virus type-1 isolates of African origin, *J. Virol.*, 69(1):263-271.
Mannstadt et al., (1999), Receptors for PTH and PTHrP: their biological importance and functional properties, *Am. J. Physiol.*, 277(5 Pt. 2):F665-675.
McCoy et al., (2005), Likelihood-enhanced fast translation functions, *Acta Crytallogr, Sect D*, 61:458-464.
Mitsukawa et al., (2008) Galanin, galanin receptors and drug targets, *Cell. Mol. Life Sci.* 65(12):1796-17805.
Müller et al., (1993) Two-Step Binding Mechanism of Fibrinogen to αIIbβ3 Integrin Reconstituted into Planar Lipid Bilayers, *J. Biol. Chem.*, 268(9):6800-6808.
Murray and Gellman, (2005), Application of Microwave Irradiation to the Synthesis of 14-helical Beta Peptides, *Organic Letters*, 7(8), 1517-1520.
Murray et al., (2005), Efficient synthesis of a beta-peptide combinatorial library with microwave irradiation, *Journal of the American Chemical Society*, 127(38), 13271-80.
Murshudov et al., (1997), Refinement of macromolecular structures by the maximum-likelihood method, *Acta Crystallogr*, Sect D 53:240-255.
Nishikawa et al., (2009), Electrostatically constrained alpha-helical peptide inhibits replication of HIV-1 resistant to enfuvirtide, *Int. J. Biochem. Cell Biol.*, 41:891-9.
Potocky et al., (2005), Effects of Conformational Stablity and Geometry of Guanidinium Display on Cell Entry by Beta-Peptides, *Journal of the American Chemical Society*, 127(11), 3686-7.
Price et al., (2007), Discrete Heterogeneous Quarternary Structure Formed by α/β-Peptide Foldamers and α-Peptides, *J. Am. Chem. Soc.*, 129:6376-6377.
Roehrl et al., (2004), A General Framework for Development and Data Analysis of Competitive High-Throughput Screens for Small-Molecule Inhibitors of Protein-Protein Interactions by Fluorescence Polarization, *Biochemistry*, 43:16056-16066.
Sadowsky et al., (2005), Chimeric (r/â + r)-Peptide Ligands for the BH3-Recognition Cleft of Bcl-xL: Critical Role of the Molecular Scaffold in Protein Surface Recognition, *J. Am. Chem. Soc.*, 127:11966-11968.

(56) References Cited

OTHER PUBLICATIONS

Sadowsky et al., (2007), (r/â+r)-Peptide Antagonists of BH3 Domain/Bcl-xL Recognition: Toward General Strategies for Foldamer-Based Inhibition of Protein-Protein Interactions, *J. Am. Chem. Soc.*, 129:139-154.

Sadowsky et al., (2007b), Exploration of Backbone Space in Foldamers Containing α- and β- Amino Acid Residues: Developing Protease-Resistant Oligomers that Bind Tightly to the BH3-Recognition Cleft of Bcl-$x_L$, *ChemBioChem*, 8:903-916.

Schmitt et al., (2004), Unexpected Relationships between Structure and Function in α,β-Peptides: Antimicrobial Foldamers with Heterogeneous Backbones, *J. Am. Chem. Soc..*, 126:6848-6849.

Schmitt et al., (2005), Residue requirements for helical folding in short alpha/beta-peptides: crystallographic characterization of the 11-helix in an optimized sequence, *Journal of the American Chemical Society*, 127(38), 13130-1.

Schmitt et al., (2006), New Helical Foldamers: heterogeneous Backbones with 1:2 and 2:1 α:β-Amino Acid Residue Patterns, *J. Am. Chem. Soc.*, 128:4538-4539.

Seebach et al., (1996), β-Peptides: Synthesis by Arndt-Eistert Homologation with Concomitant Peptide Coupling. Structure Determination by NMR and CD Spectroscopy and by X-Ray Crystallography. Helical Secondary Structure of a β-Hexapeptide in Solution and Its Stability towards Pepsin, *Helv. Chim. Acta.* 79:913-941.

Seebach et al., (1996b), Probing the Helical Secondary Structure of Short-Chain β-Peptides, Helv. Chim, Acta. 79:2043-2066.

Shortle et al., (1988), Stability Mutants of Staphylococcal Nuclease: Large Compensating Enthalpy-Entropy Changes for the Reversible Denaturation Reaction, *Biochemistry*, 27:4761-4768.

Steger et al., (2006), Kinetic dependence to HIV-1 entry inhibition, *J. Biol. Chem.*, 281(35):25813-25821.

Suhara et al., (1996), Synthesis of a New Carbohydrate Mimetics: "Carbopeptoid" Containing a C-1 Carboxylate and C-2 Amino Group, *Tetrahedron Lett.* 37(10):1575-1578.

Trkola et al., (1998) Neutralization sensitivity of human immunodeficiency virus type 1 primary isolates to antibodies and CD4-based reagents is independent of coreceptor usage, *J. Virol.*, 72(3):1876-1885.

Usdin et al., (2002) The Parathyroid hormone 2 (PTH2) receptor, *Recept. Channels*, 8(3-4):211-218.

Vagin et al., (1997) MOLREP: An automated program for molecular replacement, *J. Appl. Crystallogr* 30(6):1022-1025.

Waeber et al., (1988), Molecular pharmacology of 5-$HT_{1D}$ recognition sites: adioligand binding studies in human, pig and calf brain membranes, *Schmiedeberg's Arch. Pharmacol.*,337:595-601.

Wei et al., (2002) Emergence of resistant human immunodeficiency virus type 1 in patients receiving inhibitor (T-20) monotherapy, *Antimicrob Agents Chemother*, 46(6):1896-1905.

Williams et al., (1995), Successful therapy of collagen-induced arthritis with TNF receptor-IgG fusion protein and combination with anti-CD4, *Immunology*, 84:433-439.

\* cited by examiner

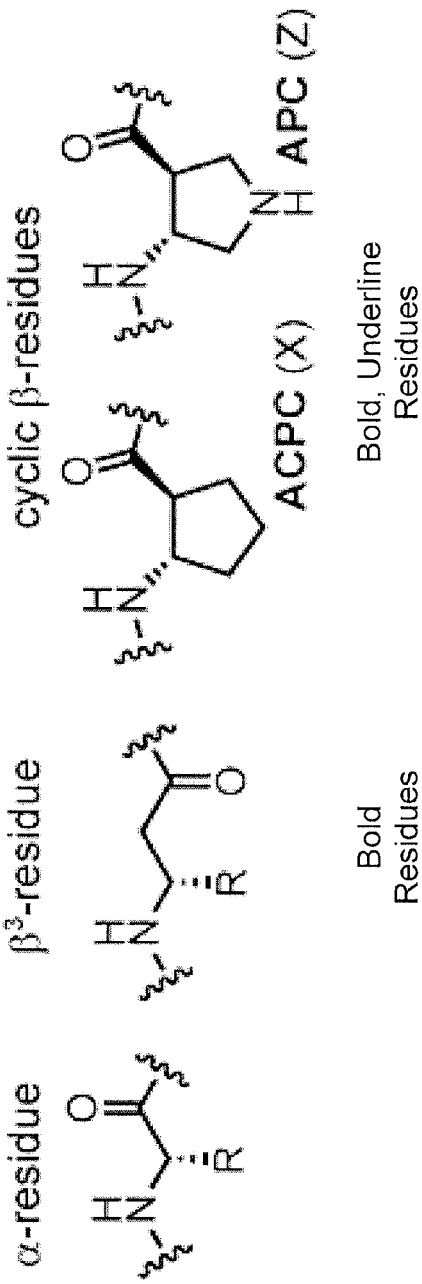

```
Ac-SGIVQQNNLLRAIEAQQHLLQLTVWGIKQLQARIL-NH2           (1)  (SEQ. ID. NO: 1)
   Ac-WMEWDREINNYTSLIHSLIEESQNQQEKNEQELL-NH2         (2)  (SEQ. ID. NO: 2)
Ac-TTWEAWDRAIAEYAARIEALIRAAQEQQEKNEAALREL-NH2        (3)  (SEQ. ID. NO: 3)
Ac-TTWEAWDRAIAEYAARIEALIRAAQEQQEKNEAALREL-NH2        (4)  (SEQ. ID. NO: 4)
Ac-TTWEAWDRAIAEYAARIEALIRAAQEQQEKNEAALREL-NH2        (5)  (SEQ. ID. NO: 5)
Ac-TTWEAWDRAIAEYAARIEALIRAAQEQQEKNEAALREL-NH2        (6)  (SEQ. ID. NO: 6)
Ac-TTWEAWDRAIAEYAXRIEXLIRAAQEQQEKNEXALREL-NH2        (7)  (SEQ. ID. NO: 7)
Ac-TTWEAWDRAIAEYAXRIEXLIZAAQEQQEKNEXALREL-NH2        (8)  (SEQ. ID. NO: 8)
Ac-TTWEAWDRAIAEYAXRIEXLIZAAQEQQEKNEXALZEL-NH2        (9)  (SEQ. ID. NO: 9)
Ac-TTWEXWDRAIAEYAXRIEXLIZAAQEQQEKNEXALZEL-NH2       (10)  (SEQ. ID. NO: 10)
Ac-TTWEXWDZAIAEYAXRIEXLIZAAQEQQEKNEXALZEL-NH2       (11)  (SEQ. ID. NO: 11)
        Ac-AEYAXRIEXLIZAAQEQQEKNEXALZEL-NH2
```

FIG. 1A

FIG. 1B (A)

NHR = SGIVQQQNNLLRAIEAQQHLLQLTVWGIKQLQARIL  SEQ. ID. NO: 12
CHR = WMEWDREINNYTSLIHSLIEESQNQQEKNEQELL  SEQ. ID. NO: 13

(B) FIG. 2B

Flu-WMEWDREINNYTSLIEESQNQQEKNEQELLELDK-NH$_2$  SEQ. ID. NO: 14

(C)

$K_d = 0.4$ nM (A) 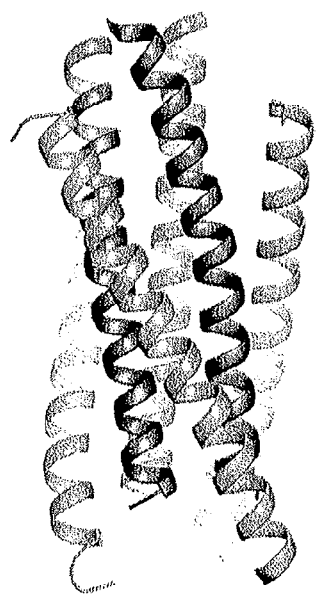
(B) 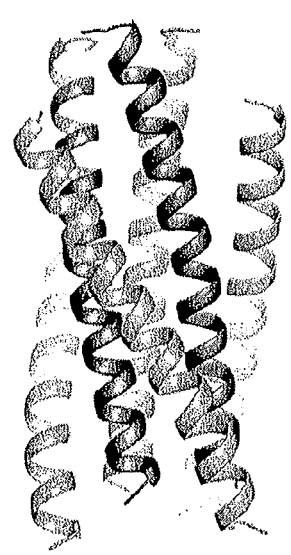
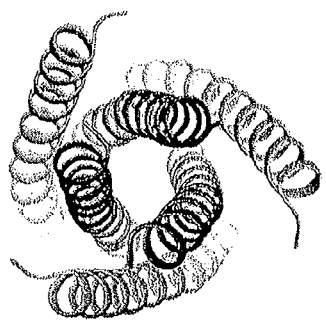
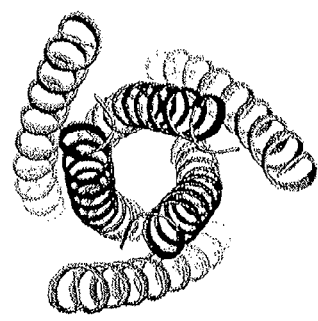
FIG. 4A    FIG. 4B

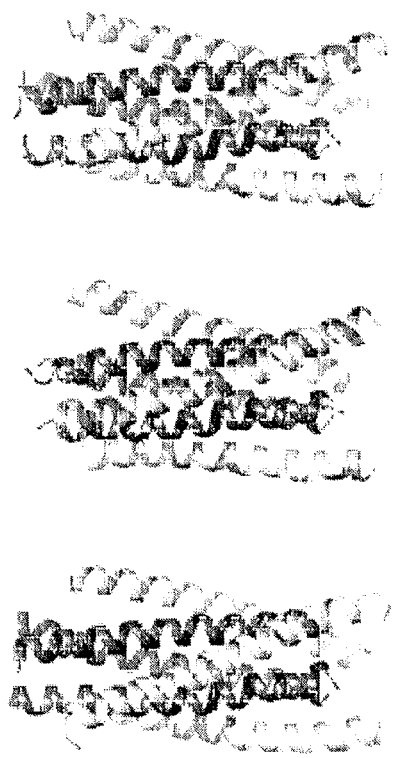
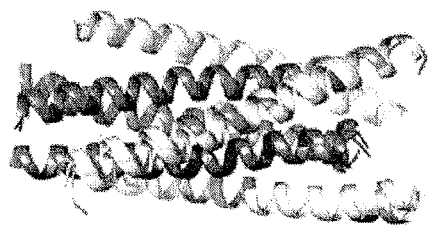
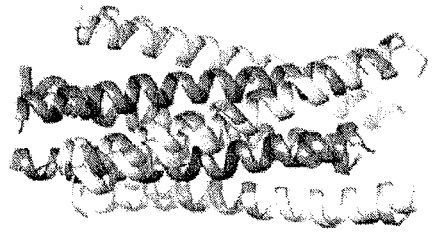

| | | |
|---|---|---|
| Ac-EEQWAREIGAQLRRMADDLNAQYERR-NH₂ | (1)' | SEQ. ID. NO: 15 |
| Ac-EEQWAREIGAQLRRMADDLNAQYERR-NH₂ | (2)' | SEQ. ID. NO: 16 |
| Ac-EEQWAREIGAQLRRMADDLNAQYERR-NH₂ | (3)' | SEQ. ID. NO: 17 |
| Ac-EEQWAREIGAQLRRMADDLNAQYERR-NH₂ | (4)' | SEQ. ID. NO: 18 |
| Ac-EEQWAREIGAQLRRMADDLNAQYERR-NH₂ | (5)' | SEQ. ID. NO: 19 |
| Ac-EEQWAREIGAQLRRMADDLNAQYERR-NH₂ | (6)' | SEQ. ID. NO: 20 |
| Ac-EEQWAREIGAQLRRMADDLNAQYERR-NH₂ | (7)' | SEQ. ID. NO: 21 |
| Ac-EEQWAREIGAQLRRMADDLNAQYERR-NH₂ | (8)' | SEQ. ID. NO: 22 |

FIG. 7A

Ac-TTWEAWDRAIAEYAARIEALIRAAQEQQEKNEAALREL-NH$_2$ (3)

*t* = 1 min

SEQ. ID. NO: 3

Ac-TTWEAWDRAIAEYAARIEALIRAAQEQQEKNEAALREL-NH$_2$ (4)

*t* = 60 min

SEQ. ID. NO: 4

Ac-TTWEXWDZAIAEYAXRIEXLIZAAQEQQEKNEXAIZEL-NH$_2$ (10)

*t* = 215 min

SEQ. ID. NO: 10

FIG. 9D

METHOD OF MAKING BIOLOGICALLY
ACTIVE ALPHA-BETA PEPTIDES

CROSS-REFERENCE TO RELATED APPLICATIONS

This is a continuation of co-pending application Ser. No. 12/578,993, filed Oct. 14, 2009, which claims priority to provisional application Ser. No. 61/106,205, filed Oct. 17, 2008, and provisional application Ser. No. 61/229,325, filed Jul. 29, 2009, both of which are incorporated herein by reference.

FEDERAL FUNDING STATEMENT

This invention was made with government support awarded under GM056414 by the National Institutes of Health The government has certain rights in the invention.

FIELD OF THE INVENTION

The invention is directed to a method of making polypeptide compounds comprising alpha- and beta-amino acid residues, the compounds produced thereby, and use of the compounds as pharmaceutically active agents to treat diseases in animals, including humans.

BACKGROUND

Many naturally occurring, biologically active compounds are proteins or peptides based upon α-amino acids (i.e., sequences of α-amino acids in which the α-carboxyl group of one amino acid is joined by an amide bond to the α-amino group of the adjacent amino acid). In recent years an approach to the discovery of new pharmaceutically active drugs has been to synthesize libraries of peptides and then to assay for compounds within the library which have a desired activity, such as a desired binding activity. However, α-amino acid peptides are not altogether satisfactory for pharmaceutical uses, in particular because they are often poorly absorbed and subject to proteolytic degradation in vivo.

Much work on β-amino acids and peptides synthesized from β-amino acids has been reported in the scientific and patent literature. See, for example, the work performed by a group led by current co-inventor Samuel H. Gellman, including: "Application of Microwave Irradiation to the Synthesis of 14-helical Beta-Peptides.," Murray & Gellman," *Organic Letters* (2005) 7(8), 1517-1520; "Synthesis of 2,2-Disubstituted Pyrrolidine-4-carboxylic Acid Derivatives and Their Incorporation into Beta-Peptide Oligomers.," Huck & Gellman, *J. Org. Chem.* (2005) 70(9), 3353-62; "Effects of Conformational Stability and Geometry of Guanidinium Display on Cell Entry by Beta-Peptides," Potocky, Menon, & Gellman, *Journal of the American Chemical Society* (2005) 127 (11):3686-7; "Residue requirements for helical folding in short alphabeta-peptides: crystallographic characterization of the 11-helix in an optimized sequence," Schmitt, Choi, Guzei, & Gellman, *Journal of the American Chemical Society* (2005), 127(38), 13130-1 and "Efficient synthesis of a beta-peptide combinatorial library with microwave irradiation," Murray, Farooqi, Sadowsky, Scalf, Freund, Smith, Chen, & Gellman, *Journal of the American Chemical Society* (2005), 127(38), 13271-80. Another group, led by Dieter Seebach in Zurich, Switzerland, has also published extensively in the beta-polypeptide field. See, for example, Seebach et al. (1996) *Helv. Chim. Acta.* 79:913-941; and Seebach et al. (1996) *Helv. Chim. Acta.* 79:2043-2066. In the first of these two papers Seebach et al. describe the synthesis and characterization of a β-hexapeptide, namely (H-β-HVal-β-HAla-β-HLeu) 2-OH. Interestingly, this paper specifically notes that prior art reports on the structure of β-peptides have been contradictory and "partially controversial." In the second paper, Seebach et al. explore the secondary structure of the above-noted β-hexapeptide and the effects of residue variation on the secondary structure.

Dado and Gellman (1994) *J. Am. Chem. Soc.* 116:1054-1062 describe intramolecular hydrogen bonding in derivatives of β-alanine and γ-amino butyric acid. This paper postulates that β-peptides will fold in manners similar to α-amino acid polymers if intramolecular hydrogen bonding between nearest neighbor amide groups on the polymer backbone is not favored.

Suhara et al. (1996) *Tetrahedron Lett.* 37(10):1575-1578 report a polysaccharide analog of a β-peptide in which D-glycocylamine derivatives are linked to each other via a C-1β-carboxylate and a C-2 α-amino group. This class of compounds has been given the trivial name "carbopeptoids."

Regarding methods to generate combinatorial libraries, several reviews are available. See, for instance, Ellman (1996) *Acc. Chem. Res.* 29:132-143 and Lam et al. (1997) *Chem. Rev.* 97:411-448.

In the recent patent literature relating to β-polypeptides, see, for example, U.S. published patent applications 2008/0166388, titled "Beta-Peptides with Antifungal Activity"; 2008/0058548, titled Concise Beta2-Amino Acid Synthesis via Organocatalytic Aminomethylation"; 2007/0154882, titled "Beta-polypeptides that inhibit cytomegalovirus infection"; 2007/0123709, titled "Beta-amino acids"; and 2007/0087404, titled "Poly-beta-peptides from functionalized beta-lactam monomers and antibacterial compositions containing same." See also U.S. published patent application 2003/0212250, titled "Peptides."

SUMMARY OF THE INVENTION

The invention is directed to a method of fabricating biologically active, proteoloytic-resistant, unnatural polypeptides. The method comprises selecting a biologically or pharmacologically active polypeptide or biologically active fragment thereof (the "target") having an amino acid sequence consisting essentially of α-amino acid residues. Then, a synthetic polypeptide is fabricated that has an amino acid sequence that corresponds to the α-amino acid sequence of the target. However, in the synthetic polypeptide, between about 14% and about 50% of the α-amino acid residues found in the target are replaced with β-amino acid residues. More preferably between about 20% and about 50% of the α-amino acid residues found in the target are replaced with β-amino acid residues. The β-amino acid residues are disposed in the synthetic polypeptide such that the β-amino acid residues and the α-amino acid residues are distributed in a repeating pattern throughout the amino acid sequence of the synthetic polypeptide. The resulting unnatural polypeptides preferably have a length of from about 10 to about 100 residues, and more preferably of from about 20 to about 50 residues. Preferably, at least two residues are β-amino acid residues.

In one version of the invention, at least one of the α-amino acid residues in the target is replaced with at least one β-amino acid residue that is cyclically constrained via a ring encompassing its $\beta^2$ and $\beta^3$ carbon atoms. In another version of the invention, most or all of the inserted β-amino acid residues are cyclically constrained via a ring encompassing its $\beta^2$ and $\beta^3$ carbon atoms. In another version of the invention, at least one of the β-amino acid residues is unsubstituted at its $\beta^2$ and $\beta^3$ carbon atoms. Alternatively all of the β-amino acid residues may substituted at their $\beta^2$ and $\beta^3$ carbon atoms (with linear, branched or cyclic substituents).

In another version of the invention between about 14% and about 50% of the α-amino acid residues found in the target are replaced with β-amino acid residues wherein each β-amino acid residue has at least one side chain identical to the α-amino acid residue it replaces. Thus, in this version, the method comprises selecting the target to be mimicked and then fabricating a synthetic polypeptide that has an amino acid sequence that corresponds to the sequence of the target, but wherein between about 20% and about 50% of the α-amino acid residues found in the target are replaced with analogous β-amino acid residues. In this version of the invention, each analogous β-amino acid residue has at least one side chain identical to the α-amino acid residue it replaces. Again, the β-amino acid residues and the α-amino acid residues are distributed in a repeating pattern in the amino acid sequence of the synthetic polypeptide.

Also included within the invention are isolated, unnatural polypeptides comprising a primary amino acid sequence as shown in SEQ. ID. NOS: 4-11, 16-22, and 25-30. These unnatural polypeptides can be used in a method of inhibiting fusion of human immunodeficiency virus to human cells. The method comprises contacting human cells with an isolated, unnatural polypeptide comprising a primary amino acid sequence as shown in SEQ. ID. NOS: 4-11, 16-22, and 25-30, whereby the cells are then resistant to entry of HIV through their cell membrane.

Another version of the invention is directed to a method of inhibiting fusion of human immunodeficiency virus (HIV) to human cells. The method comprises first selecting a natural, biologically active polypeptide or biologically active fragment thereof having an amino acid sequence comprising α-amino acid residues, and necessary for HIV fusion in vivo. A synthetic polypeptide is then fabricated that has an amino acid sequence that corresponds to the sequence of the biologically active polypeptide or fragment thereof. In the synthetic polypeptide, between about 14% and about 50% of the α-amino acid residues found in the biologically active polypeptide or fragment are replaced with β-amino acid residues. Further still, in the synthetic polypeptide the β-amino acid residues and the α-amino acid residues are distributed in a repeating pattern. Human cells are then contacted with the synthetic polypeptide.

In all embodiments of the invention, it is generally preferred (although not required) that the repeating pattern places the β-amino acid residues in alignment on one side of a helix in the unnatural polypeptides that adopt a helical conformation. That is, in the folded structure adopted by the polypeptides, the repeating pattern of α- and β-residues disposes the β-amino acid residues in alignment along one side of the folded molecular structure when the unnatural polypeptides adopt a helical conformation. The repeating pattern of β-amino acid residues and α-amino acid residues may be a pattern of from two to seven residues in length, such as (ααααααβ), (αααααβ), (ααααβ), (αααβ), (ααβ), (ααβαααβ), (ααβαβαβ), and (αβ). All unique patterns of α- and β-amino acid residues of from two to seven residues in length are explicitly within the scope of the invention.

The method can be used to fabricate polypeptide compounds via any means of polypeptide synthesis now known or developed in the future. Using current methods of peptide synthesis, polypeptides fabricated according to the present method are generally less than about 100 residues long, and more preferably from between about ten total residues and about 50 total residues, more preferably still between about 20 and about 50 total residues. Ranges above and below these stated ranges are within the scope of the invention. Many commercial services, such as Abgent (San Diego, Calif., USA) offer peptide synthesis services up to about 100 residues.

The sequence of side chains along the oligomer is preferably based on a prototype α-peptide (the target) having desirable biological activity against a disease state. The sequence of side chains may also be modified after translation onto the α/β-peptide backbone to optimize the desired properties of the compounds.

Each β-residue introduced into the unnatural α/β-peptide backbone can bear side chains at one of the two backbone carbons ($\beta^3$ or $\beta^2$) or both of the backbone carbons. The side chains may also be cyclically constrained via a ring connecting the two backbone carbons.

Of particular note in the present invention is that substitution of α-residues in the prototype target sequence with β-residues bearing side chains allows modification to the backbone without disrupting the sequence of side chains along the oligomer. Cyclic β-residues rigidify the backbone and promote helical structure.

It is preferred that β-residues be evenly spaced along the entire length of the sequence in order to maximize the protease resistance imparted to the oligomer by the backbone modifications. Examples of regularly repeating backbone patterns include, but are not limited to, (ααααααβ), (αααααβ), (ααααβ), (αααβ), (ααβ), (ααβαααβ), (ααβαβαβ), and (αβ).

Desirable properties in the final compounds include the ability to modulate a protein-protein interaction involved in the genesis or progression of a disease state in general and HIV entry into human cells in particular, and improved pharmacokinetic and pharmacodynamic properties relative to the target α-peptide sequence (e.g., better in vivo half-life, biodistribution, etc.). Many of the final compounds adopt a helical structure in solution, although a helical structure is not required.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods, compounds, and compositions of the present invention can comprise, consist of, or consist essentially of the essential elements and limitations of the invention as described herein, as well as any additional or optional ingredients, components, or limitations described herein or otherwise useful in synthetic organic chemistry.

BRIEF DESCRIPTION OF THE DRAWINGS

FIG. 1A depicts sequences of α-peptides 1-3 and α/β-peptides 4-11. Bold residues indicate $\beta^3$-residues corresponding to their α-amino acid counterparts; bold, underline residues are the cyclically constrained β-amino acid residues ACPC (X) and APC (Y). FIG. 1B depicts structures of an α-amino acid, the corresponding $β^3$-amino acid analog, and cyclic β-residues ACPC (X) and APC (Z).

Figure 2C:
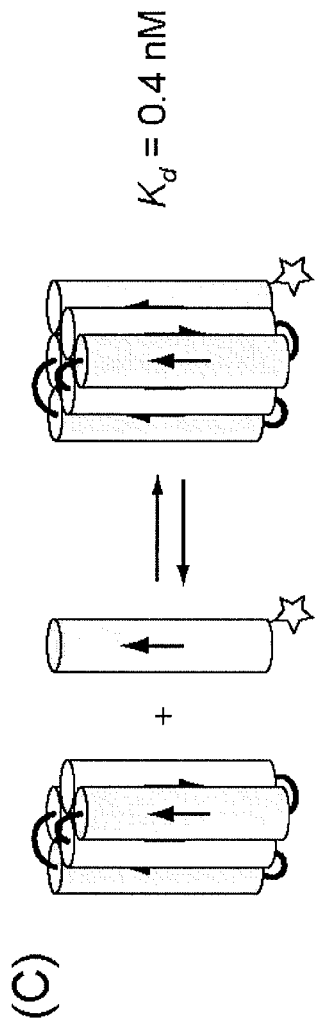

FIG. 2A depicts the gp41-5 protein, composed of three NHR segments and two CHR segments. FIG. 2B depicts the fluorescent CHR peptide used as a tracer in competition FP assays (Flu=5-carboxyfluorescein). FIG. 2C is a schematic of the interaction between the Flu-CHR peptide and the 5-helix bundle formed by gp41-5.

Figure 3A:
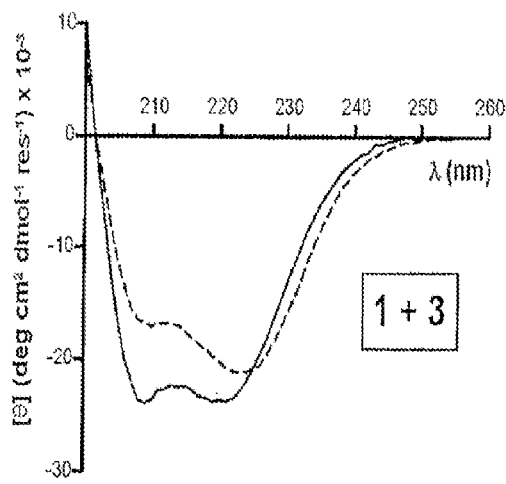
Figure 3B:
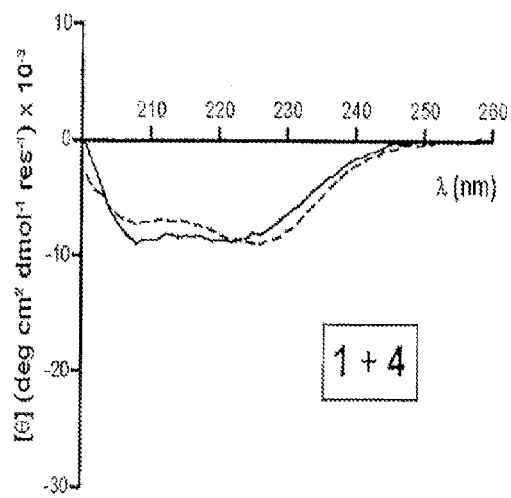
Figure 3C:
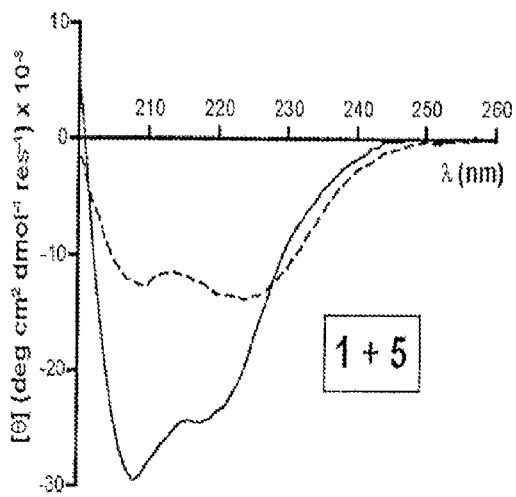
Figure 3D:
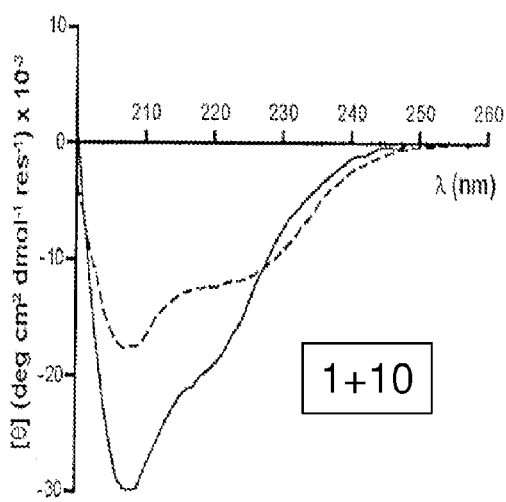

FIGS. 3A, 3B, 3C, and 3D depict circular dichroism (CD) spectra of complexes formed between NHR peptide 1 and CHR analogs 3 (FIG. 3A), 4 (FIG. 3B), 5 (FIG. 3C), and 10 (FIG. 3D). Solid lines are spectra observed for a 1:1 mixture of the indicated oligomers at a total concentration of 20 μM in PBS at 25° C. Dashed lines are the spectra calculated for 1:1 non-interacting mixtures from CD of the individual components.

FIGS. 4A and 4B are a comparison of the six-helix bundles observed in the crystal structures of the newly characterized complex between α-peptides 1 and 3 (FIG. 4A) and the previously characterized complex between α-peptides 1 and 2 (FIG. 4B) (Chan, Fass, Berger, and Kim, *Cell* 1997, 89, 263-273). The RMSD of $C_α$ atoms between the two structures is 0.7 Å. FIG. 4C depicts the crystal structure of the 1+3 complex. FIG. 4D depicts the crystal structure of the 1+10 complex solved to 2.8 Å resolution. FIG. 4E depicts the crystal structure of the 1+8 complex solved to 2.8 Å resolution. FIGS. 4F and 4G depict overlays of the all-α-peptide helix bundle-formed 1+3 with that formed by 1+10 (FIG. 4F) and 1+8 (FIG. 4G).

Figure 5A:
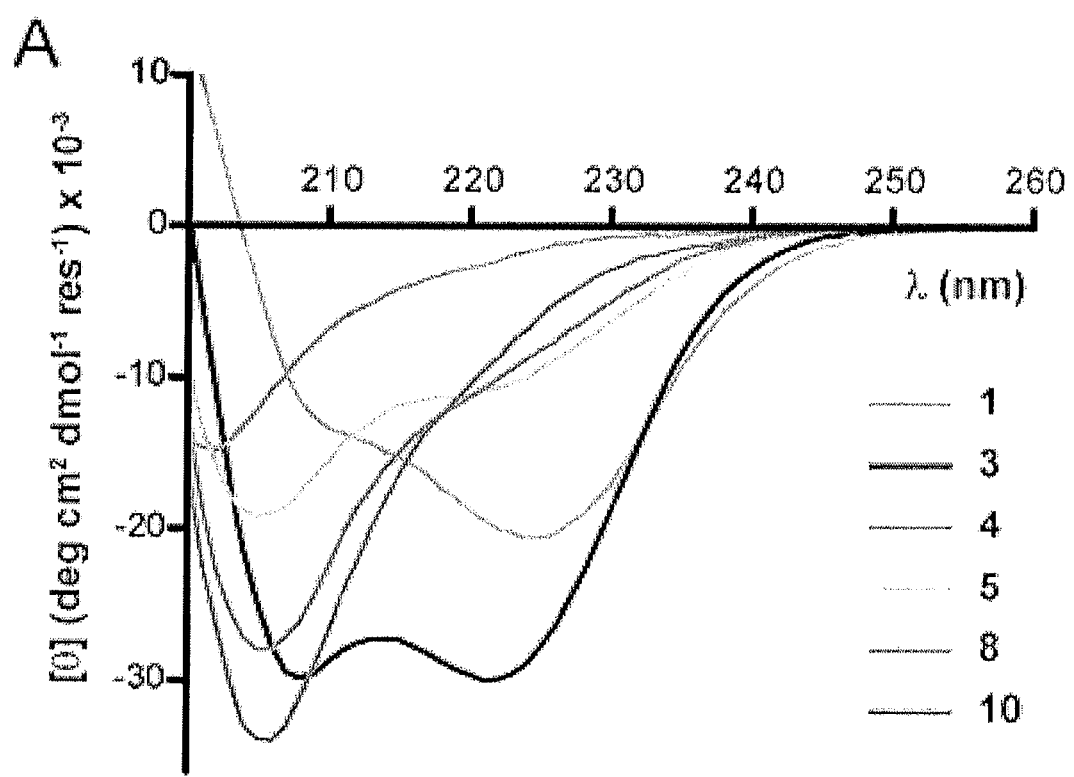
Figure 5B:
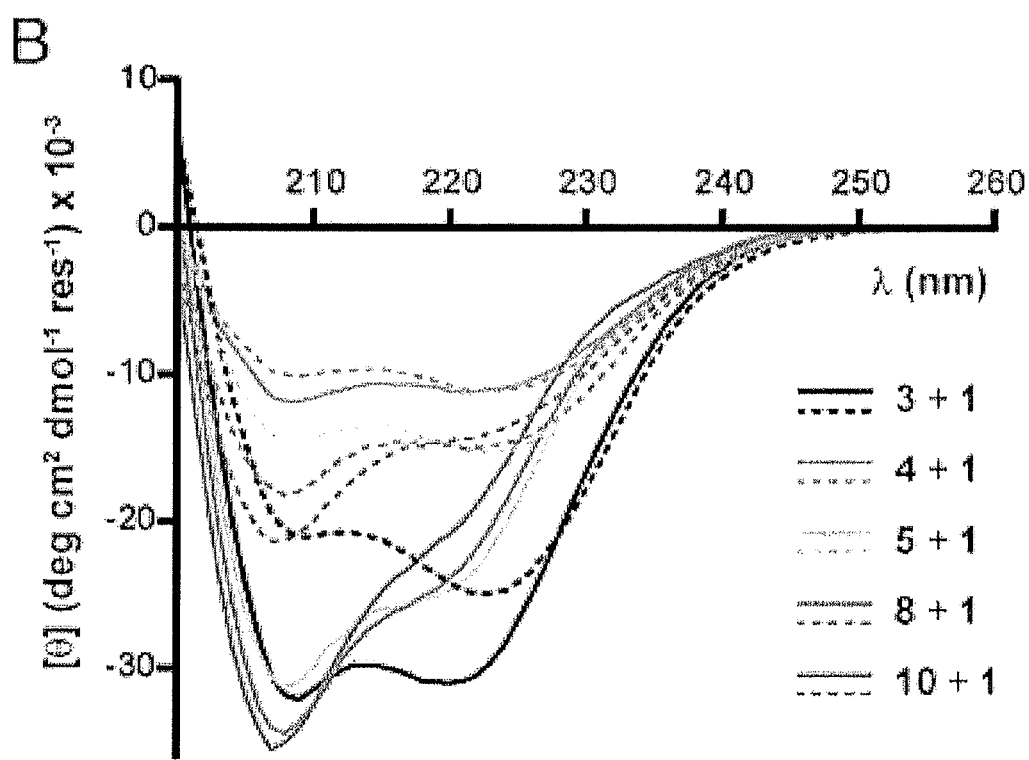
Figure 5C:
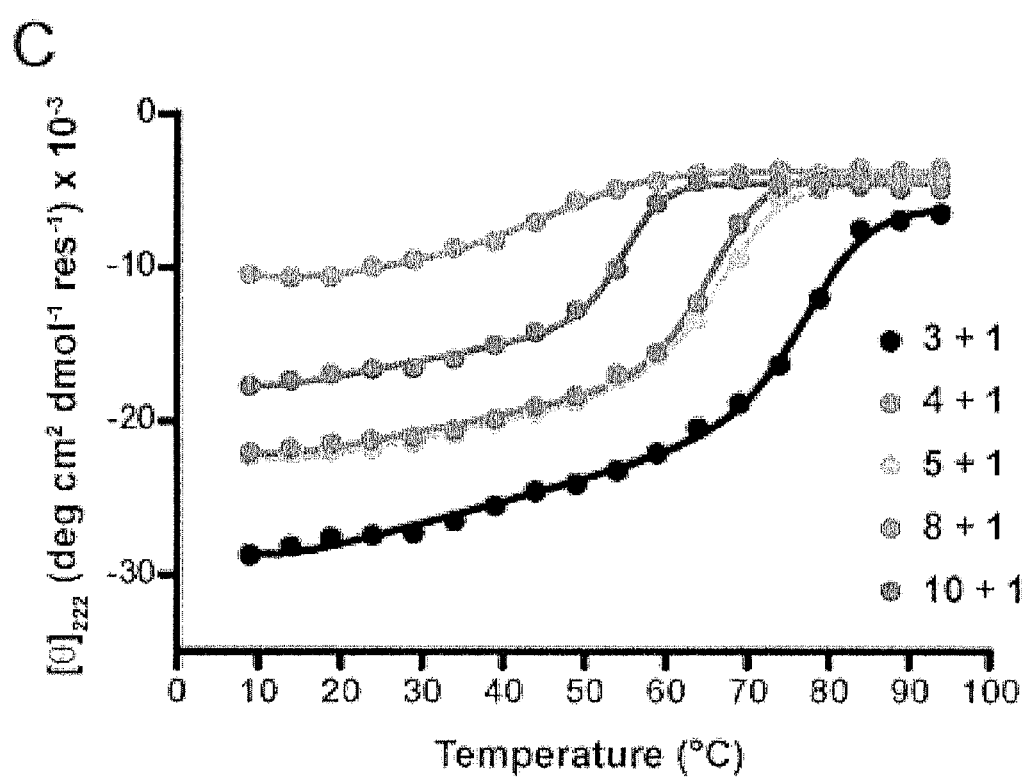

FIGS. 5A, 5B, and 5C depict circular dichroism (CD) spectra. FIG. 5A depicts superimposed CD data for NHR peptide 1 and CHR peptides 3, 4, 5, 8 and 10 at 20 μM concentration in PBS at 25° C. FIG. 5B depicts CD spectra of the indicated 1:1 mixtures at a total concentration of 20 μM in PBS at 25° C. (solid lines) along with the spectra calculated for 1:1 non-interacting mixtures from CD measurements on the individual components (dashed lines). FIG. 5C depicts temperature-dependent molar ellipticity at 222 nm for the indicated complexes at 20 μM concentration in PBS.

Figure 6:
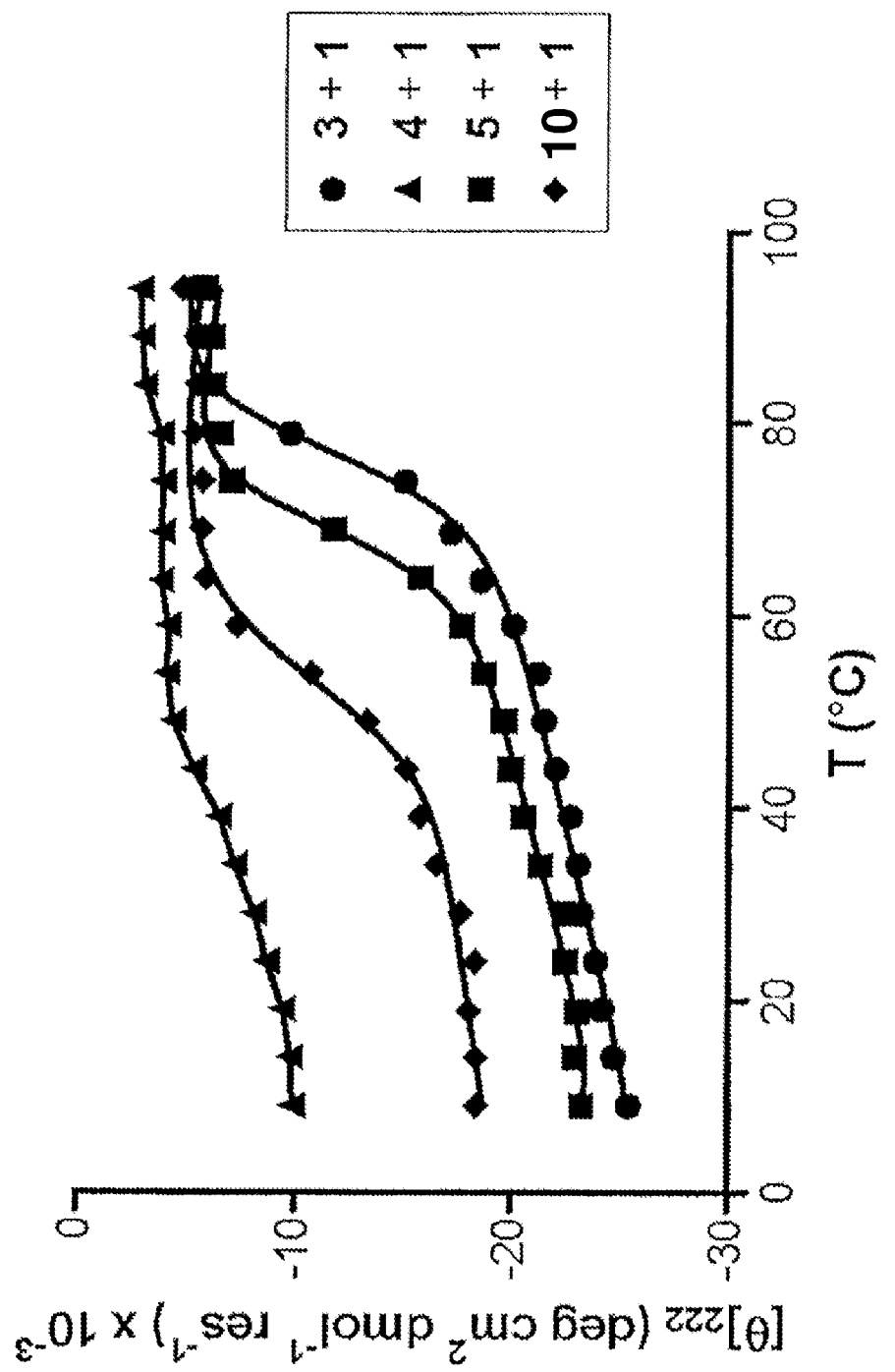

FIG. 6 is a graph depicting temperature dependent molar ellipticity at 222 nm for 1:1 mixtures of 1+3, 1+4, 1+5 and 1+10 at 20 μM total peptide in PBS.

Figure 7B:
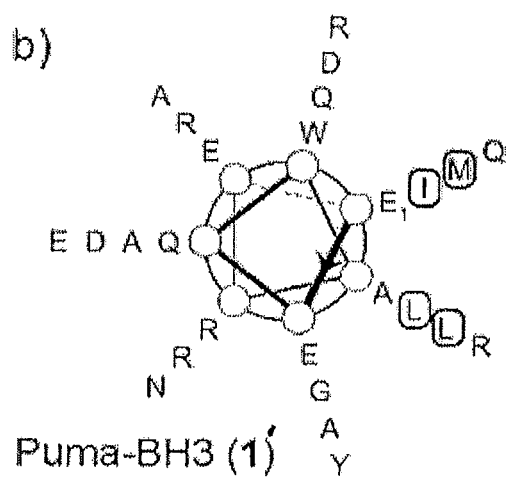
Figure 7C:
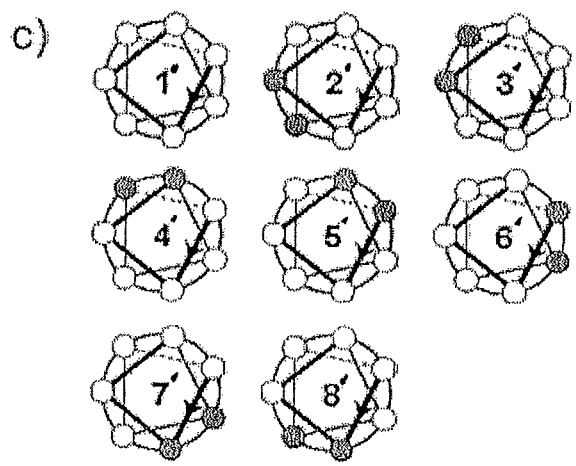
Figure 7D:

FIG. 7A depicts the primary sequence of the Puma BH3 peptide (1') and α/β-peptide analogs 2'-8' (gray circles and bold letters indicate $β^3$ residues). FIG. 7B depicts a helical wheel diagram of 1'. Boxed residues in FIGS. 7A and 7B indicate hydrophobic positions most important for binding based on sequence homology. FIG. 7C presents schematic representations of 1'-8', drawn in the same orientation as in FIG. 7B; white and gray circles indicate heptad positions occupied by α-residues and $β^3$-residues, respectively. FIG. 7D presents the structures of a generic α-amino acid and a generic $β^3$-amino acid; the "R" substituent is conventionally referred to as the "side-chain."

Figure 8:
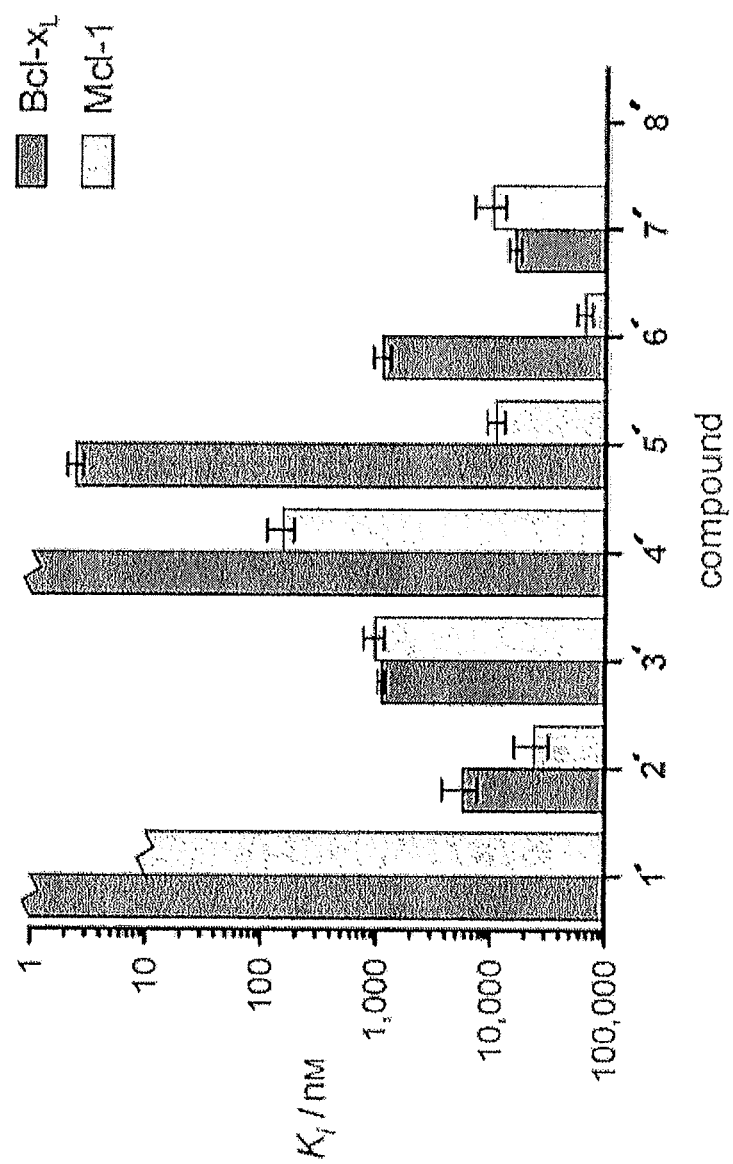

FIG. 8 is a histogram depicting inhibition constants for displacement of a fluorescently labeled Bak BH3 peptide bound to Bcl-$x_L$ or Mcl-1 by compounds 1'-8'. Broken bars indicate compounds binding tighter than discernable in the assay. The values for 8' were weaker than 100 μM for both proteins.

Figure 9A:
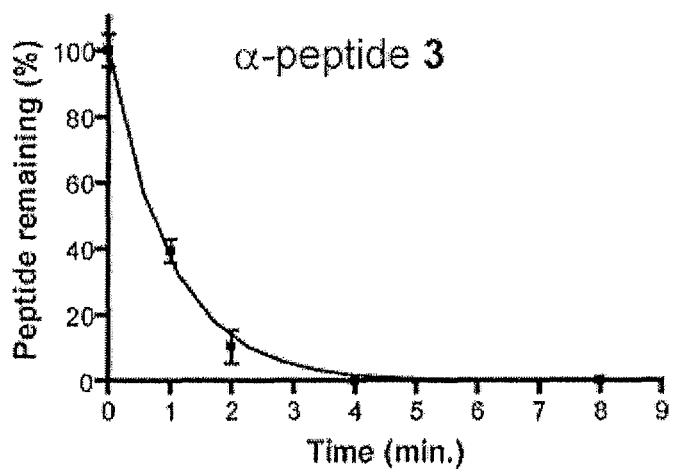
Figure 9B:
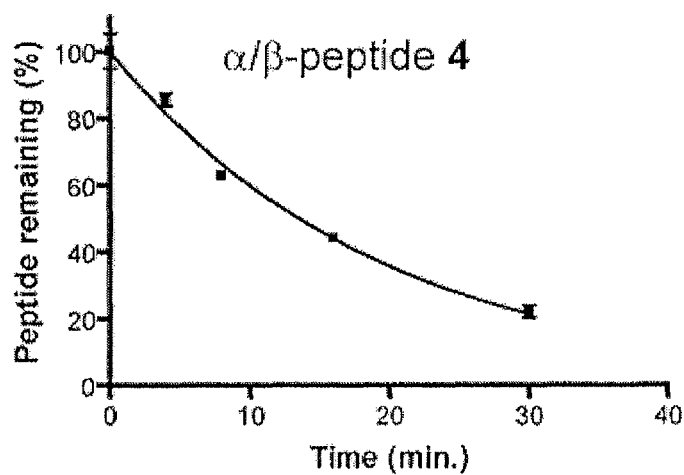
Figure 9C:
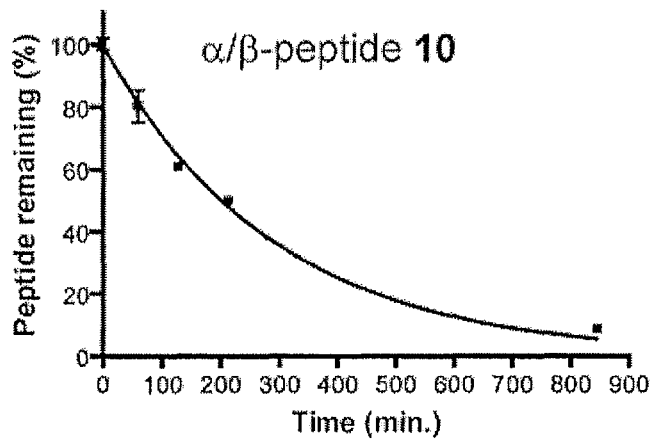

FIGS. 9A, 9B, and 9C depict proteolytic stability of 3, 4 and 10, respectively, whose structures are shown in FIG. 9D. Solutions of 20 μM peptide in TBS were incubated at room temperature with 10 μg/mL proteinase K. FIGS. 9A, 9B, and 9C depict time-dependent degradation data with curves resulting from fits to a simple exponential decay. FIG. 9D shows the structure of compounds 3, 4, and 10 and also depicts proteolysis products observed by mass spectrometry at the indicated time point. Vertical lines indicate observation by MALDI-MS of one or both products consistent with hydrolysis of the backbone amide bond between the indicated residues.

Figure 10A:
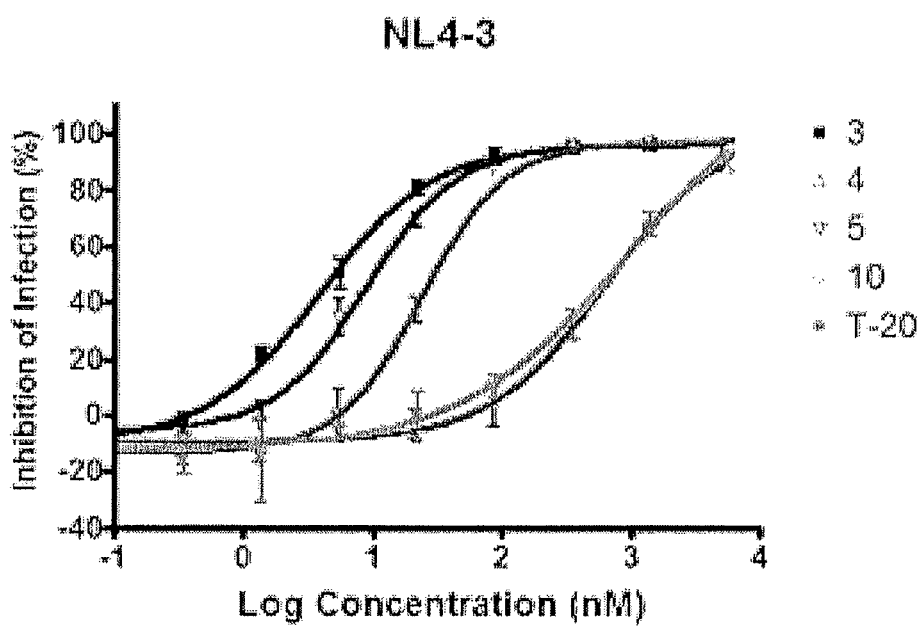
Figure 10B:
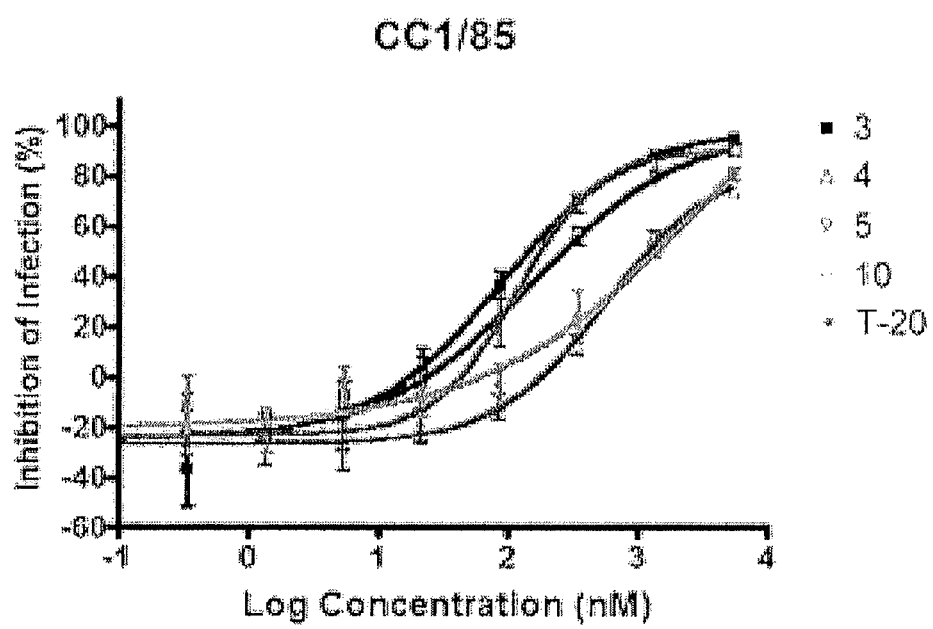
Figure 10C:
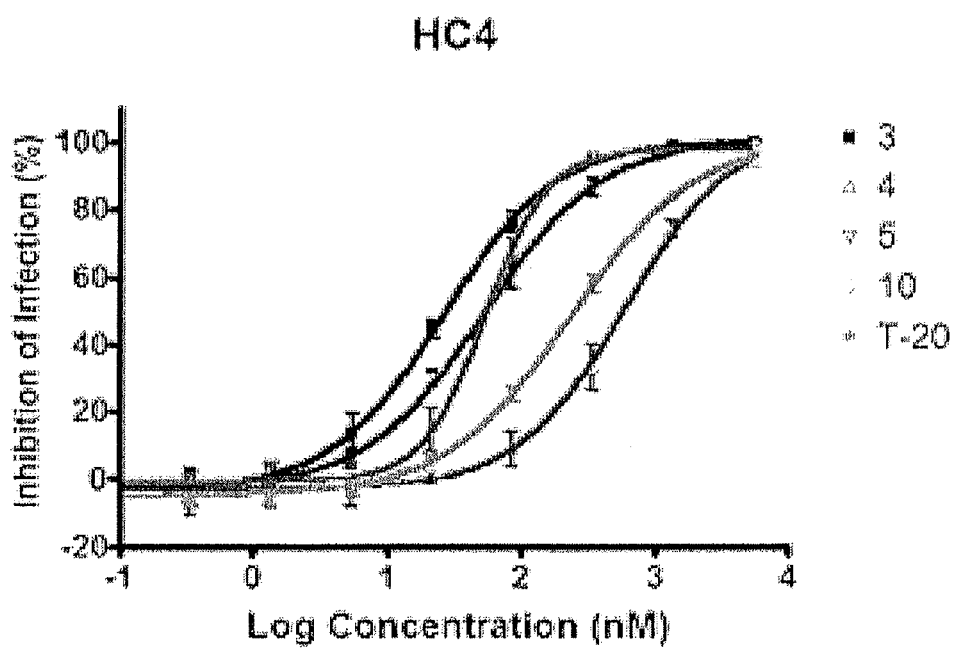
Figure 10D:
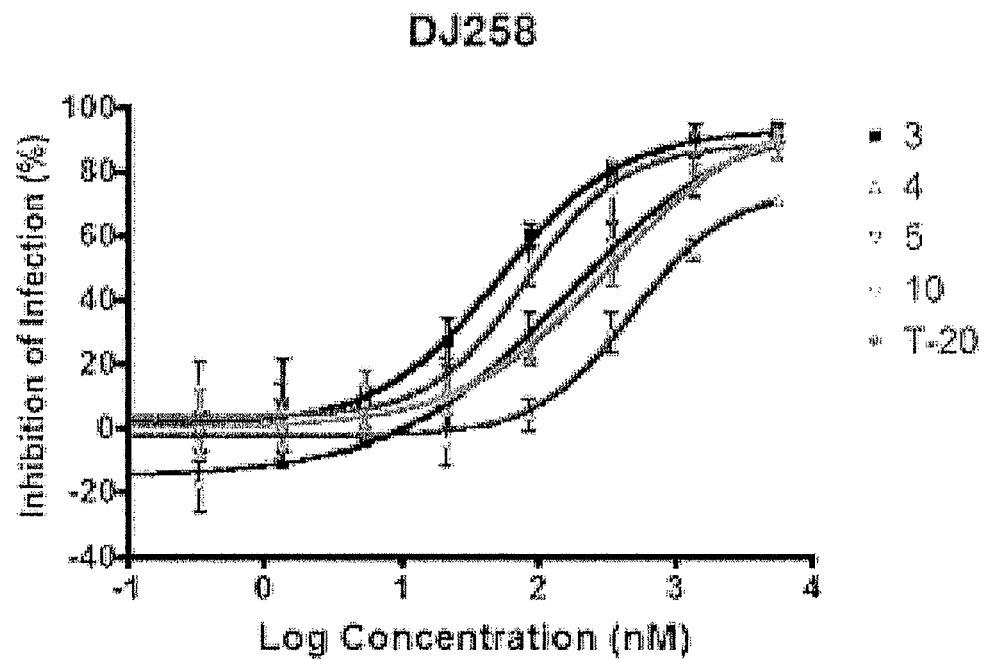

FIGS. 10A, 10B, 10C, and 10D are graphs depicting inhibition of infection of TZM-bl cells by the indicated virus strains as a function of the concentration of gp41-derived fusion-blocking peptides. Each data point is the mean±S.E.M. from three independent experiments. FIG. 10A depicts inhibition of NL4-3 infection. FIG. 10B depicts inhibition of CC1/85 infection. FIG. 10C depicts inhibition of HC4 infection. FIG. 10D depicts inhibition of DJ258 infection.

DETAILED DESCRIPTION

The following abbreviations are used throughout the specification:
$Ac_2O$=acetic anhydride, acetic oxide, acetylacetate.
ACPC=trans-2-aminocyclopentanecarboxylic acid.
APC=trans-3-aminopyrrolidine-4-carboxylic acid.
Boc=tert-butoxycarbonyl.
BOP=benzotriazole-1-yl-oxy-tris-(dimethylamino)-phosphonium hexafluorophosphate.
β-Gal=β-galactosidase.
CD=circular dichroism.
CHR=C-terminal heptad repeat.
DIEA=N,N-diisopropylethylamine.
DMF=dimethylformamide.
DMSO=dimethylsulfoxide.
EDTA=ethylenediaminetetraacetic acid.
FKBP=FK506-binding protein.
Fmoc=9-fluorenylmethyl formyl.
FP=fluorescence poloarization.
Halogen=F, Cl, Br and I.
HBTU=2-(1H-benzotriazole-1-yl)-1,1,3,3-tetramethylaminium hexafluoro-phosphate.
HIV=human immunodeficiency virus.
HOBT=N-hydroxybenzotriazole.
HPLC=high-performance liquid chromatography.
$iPr_2EtN$=N,N-diisopropylethylamine.
IPTG=isopropyl β-D-1-thiogalactopyranoside.
MALDI-TOF-MS=matrix-assisted, laser-desorption, time-of-flight mass spectrometry.
MeOH=methanol.
NHR=N-terminal heptad repeat.
NMP=1-Methyl-2-pyrollidinone.
PTH1R and PTH2R=parathyroid hormone receptors 1 and 2.
RMSD=root mean square deviation.
RTKs=receptor tyrosine kinases.
TNF=tumor necrosis factor.
PBS=phosphate-buffered saline.
TBS=tris-buffered saline.
Tris=tris(hydroxymethyl)aminomethane.
TFA=trifluoroacetic acid.
TNBS=2,4,6-trinitrobenzene-sulfonic acid.

In the present description unless otherwise indicated terms such as "compounds of the invention" embrace the compounds in salt form as well as in free base form and also when the compounds are attached to a solid phase. Where a basic substituent such as an amine substituent is present, the salt form may be an acid addition salt, for example a dihydrochloride. Salts include, without limitation, those derived from mineral acids and organic acids, explicitly including hydrohalides, e.g., hydrochlorides and hydrobromides, sulfates, phosphates, nitrates, sulfamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulfonates, ethanesulfonates, benzenesulfonates, p-toluenesulfonates, cyclohexylsulfamates, quinates, and the like. Base addition salts include those derived from alkali or alkaline earth metal bases or conventional organic bases, such as triethylamine, pyridine, piperidine, morpholine, N methylmorpholine, and the like. Other suitable salts are found in, for example, Handbook of Pharmaceutical Salts, P. H. Stahl and C. G. Wermuch, Eds., © 2002, Verlag Helvitica Chemica Acta (Zurich, Switzerland) and S. M. Berge, et al., "Pharmaceutical Salts," *J. Pharm. Sci.*, 66: p. 1-19 (January 1977), both of which are incorporated herein by reference.

The β-amino acid residues of the β-peptides of the invention are characteristically β-amino-n-propionic acid derivatives, typically further substituted at the 2-position carbon atom (the ($\beta^2$ carbon) and/or the 3-position carbon atom (the $\beta^3$ carbon) in the backbone and may be further substituted, e.g., at the N-terminal amino nitrogen atom. The $\beta^2$, $\beta^3$, and amino substituents may include substituents containing from 1 to 43 carbon atoms optionally interrupted by up to 4 hetero atoms, selected from O, N or S, optionally containing a carbonyl (i.e., —C(O)—) group, and optionally further substituted by up to 6 substituents selected from halo, $NO_2$, —OH, $C_{1-4}$ alkyl, —SH, —$SO_3$, —$NH_2$, $C_{1-4}$-acyl, $C_{1-4}$-acyloxy, $C_{1-4}$-alkylamino, $C_{1-4}$-dialkylamino, trihalomethyl, —CN, $C_{1-4}$-alkylthio, $C_{1-4}$-alkylsulfinyl, or $C_{1-4}$-alkylsulfonyl.

Substituents on the $\beta^2$ and/or $\beta^3$ carbon atoms of β-amino acid residues may be selected from the group comprising the substituents which are present on the α-carbon atoms of natural α-amino acids, e.g., —H, —$CH^3$, —$CH(CH_3)_2$, —$CH_2$—$CH(CH_3)_2$, —$CH(CH_3)CH_2CH_3$, —$CH_2$-phenyl, —$CH_2$-pOH-phenyl, —$CH_2$-indole, —$CH_2$—SH, —$CH_2$—$CH_2$—S—$CH_3$, —$CH_2$OH, —CHOH—$CH_3$, —$CH_2$—$CH_2$—$CH_2$—$CH_2$—$NH_2$, —$CH_2$—$CH_2$—$CH_2$—NH—C(NH)$NH_2$, —$CH_2$-imidazole, —CH—COOH, —$CH_2$—$CH_2$—COOH, —$CH_2$—$CONH_2$, —$CH_2$—$CH_2CONH_2$ or together with an adjacent NH group defines a pyrrolidine ring, as is found in the proteinogenic α-amino acid proline.

In accordance with the present invention it has been found that the compounds of the invention have desirable properties. For example, compounds described herein having approximately seven or more residues, three or more of which are cyclically constrained, are able to form stable helix structures in solution. Also the compounds described herein have much greater stability to the action of peptidases, such as pepsin, than do their corresponding α-peptides. As such the compounds described herein are expected exhibit correspondingly longer half lives, e.g., serum half lives, in vivo than corresponding α-peptides.

The invention includes the compounds of the invention in pure isomeric form, e.g., consisting of at least 90%, preferably at least 95% of a single isomeric form, as well as mixtures of these forms. The compounds of the invention may also be in the form of individual enantiomers or may be in the form of racemates or diastereoisomeric mixtures or any other mixture of the possible isomers.

The compounds of the invention may be prepared by the synthetic chemical procedures described herein, as well as other procedures similar to those which may be used for making α-amino acid peptides. Such procedures include both solution and solid phase procedures, e.g., using both Boc and Fmoc methodologies. Thus the compounds described herein may be prepared by successive amide bond-forming procedures in which amide bonds are formed between the β-amino group of a first β-amino acid residue or a precursor thereof and the α-carboxyl group of a second β-amino acid residue or α-amino acid residue or a precursor thereof. The amide bond-forming step may be repeated as many times, and with specific α-amino acid residues and/or β-amino acid residues and/or precursors thereof, as required to give the desired α/β-polypeptide. Also peptides comprising two, three, or more amino acid residues (α or β) may be joined together to yield larger α/β-peptides. Cyclic compounds may be prepared by forming peptide bonds between the N-terminal and C-terminal ends of a previously synthesized linear polypeptide.

$\beta^3$-amino acids may be produced enantioselectively from corresponding α-amino acids; for instance, by Arndt-Eisert homologation of N-protected α-amino acids. Conveniently such homologation may be followed by coupling of the reactive diazo ketone intermediate of the Wolff rearrangement with a β-amino acid residue.

The method described herein can be used to establish discrete compound collections or libraries of compounds for use in screening for compounds having desirable activities, in particular biological activities indicative of particular pharmaceutical uses.

Thus the invention also includes discrete compound collections (typically comprising from 2 to about 1000 compounds) and libraries of compounds (typically comprising from 20 to 100 compounds up to many thousands of compounds, e.g., 100,000 compounds or more) comprising pluralities of the compounds described herein.

Compounds having desired biological activities may be identified using appropriate screening assays as described below.

The HIV protein gp41 is a canonical example of a class of proteins involved in the fusion of enveloped viruses to mammalian cells. During virus-cell fusion, the gp41 N-terminus inserts into the host cell membrane, and the trimeric protein undergoes a drastic structural rearrangement involving the formation a six-helix bundle composed of three copies of a N-terminal heptad repeat (NHR) domain and three copies of a C-terminal heptad repeat (CHR) domain. Formation of the gp41 six-helix bundle is an essential step for virus-cell fusion, and is therefore an attractive process to target for interruption using a rationally designed antiviral agent. To demonstrate the utility and functionality of the present invention, unnatural polypeptides analogous to gp41, but comprised of mixtures of α- and β-residues (α/β-peptides) were fabricated and shown to act as inhibitors of HIV-cell fusion.

A number of α-peptides based on either gp41 NHR or CHR sequences, e.g., compounds 1 and 2, (SEQ. ID. NOS: 1 and 2 respectively, see FIG. 1A) have been investigated as fusion inhibitors. The most prominent example is the 36-residue α-peptide drug enfuvirtide (sold by Hoffmann-La Roche, Inc. under the registered trademark "FUZEON"), which is derived from the CHR domain. Several groups have tried to inhibit gp41 six-helix bundle formation with short α-helix mimics, including small molecules, cyclic peptides, terphenyls and β-peptides, that are intended to display three key CHR hydrophobic side chains in an α-helix-like fashion; however, these molecules display only modest anti-HIV activity in cell-based assays ($IC_{50}$>1 μM vs.~1 nM for enfuvirtide). Similar results have been seen with relatively short α-peptides that have been chemically predisposed toward α-helicity by internal cross-links.

The present inventors have discovered that systematically developing α/β-peptide foldamers that mimic key structural and functional properties of prototype α-peptide sequences, yields biologically active, unnatural polypeptides that are more stable to proteolytic degradation than analogous α-polypeptides. The method, referred to herein as "sequence-based design," involves the systematic substitution of α-residues throughout a target sequence with β-amino acid residues in general, and preferably $β^3$-amino residues bearing the side chain of the replaced α-residue. See FIG. 1B. The α→β modification alters the peptide backbone chemical composition while retaining the side chain sequence from the parent α-peptide. The systematic use of sequence-based design generates α/β-peptides that exhibit complex behaviors such as formation of protein-like quaternary assemblies and mimicry of protein helices involved in apoptosis. gp41-Mediated HIV-cell fusion was chosen as a model system to demonstrate the utility and functionality of sequence-based backbone modification because the target is of great biomedical importance. In short, a pharmacologically active agent that inhibits gp41-mediated HIV-cell fusion, designed using a rational and systematic method that can be repeated for other therapeutically important targets, is incredibly useful. The method provides an avenue to design pharmacologically active agents in less time, with less trial and error, and in a rational, directed fashion.

α-Peptides based on the native gp41 CHR sequence, such as compound 2, have been widely studied, and several groups have published efforts to improve the binding affinity and biological stability of CHR α-peptides by rational mutagenesis. To demonstrate the utility and functionality of the present invention, a recently reported gp41 CHR analog, α-peptide 3 (SEQ. ID. NO: 3, see FIG. 1A) was chosen as the starting point for α→β modification. α-Peptide 3 includes numerous side chain mutations intended to enhance helical propensity by engineered intrahelical salt bridges and Xxx→Ala substitutions. In previous studies, 3 showed enhanced antiviral efficacy in cell culture and increased half-life relative to peptides based on the wild-type CHR sequence. Although the mutations in 3 were not intended to modify the structural nature of its binding interactions with the gp41 NHR domain, additional experimental evidence was sought that the six-helix bundle structure was unchanged. A co-crystal of α-peptides 1 and 3 was obtained by hanging drop vapor diffusion and the structure was solved to 2.0 Å resolution (see Table 1 and FIG. 4A). The resulting six-helix bundle is essentially identical to that formed by native NHR+CHR peptide complex. Compare FIG. 4A (the 1+3 co-crystal and FIG. 4B (the 1+2 co-crystal).

TABLE 1

Crystal Data Collection and Refinement Statistics.*

|  | 1 + 3 complex |
|---|---|
| Data Collection | |
| Resolution (Å) | 44.8-2.0 (2.1-2.0) |
| Total observations | 137,233 |
| Unique observations | 15,938 |
| Redundancy | 8.6 (3.6) |
| Completeness (%) | 99.9 (100) |
| I/σ | 28.0 (4.7) |
| $R_{sym}$† (%) | 5.0 (26.2) |
| Refinement | |
| Resolution (Å) | 25.0-2.0 |
| R (%) | 21.1 |
| $R_{free}$‡ (%) | 26.0 |
| Avg. B factor (Å$^2$) | 18.6 |
| RMSD | |
| Bonds (Å) | 0.013 |
| Angles (°) | 1.1 |

*Values in parentheses are for data from the highest resolution shell;
†$R_{sym} = Σ_n|I_n - <I>|/Σ_n I_n$ where $I_n$ is the intensity of an independent observation of reflection n and <I> is the average of multiply recorded and symmetry related observations of reflection n;
‡Free R reflections (~5% of total reflections) were held aside throughout refinement.

Among a variety of different α/β backbone patterns examined by the present inventors for use in sequence-based design, the most widely studied has been the ααβαααβ repeat. This pattern, which is tuned to the seven-residue repeat of the α-helix, places one β-residue per helical turn and results in a "stripe" of β-residues along one face of the helix. Crystal structures have shown that the helices formed by the ααβαααβ backbone are highly homologous to the α-helix. In the initial attempt at α→β modification of 3, eleven $β^3$-residues were incorporated in an ααβαααβ pattern (α/β-peptide 4, SEQ. ID. NO: 4, see FIG. 1A). This resulted in the non-natural residues occupying positions opposite the hydrophobic face involved in binding to the gp41 NHR core.

To determine the affinity of α-peptide 3 and α/β analogues for gp41, a recently reported in vitro competition fluorescence polarization (FP) assay was employed. The assay uses a protein model of the gp41 fusion intermediate. See FIGS. 2A, 2B, and 2C. The model protein, gp41-5, is composed of three NHR segments (SEQ. ID. NO: 12) and two CHR segments (SEQ. ID. NO: 13) linked by short flexible loops. See FIG. 2A. The gp41-5 construct folds to form a five-helix bundle with a single binding site for a fluorescein-labeled CHR α-peptide. The fluorescein-labeled CHR α-peptide (SEQ. ID. NO: 14) is shown in FIG. 2B. Displacement of this fluorescent ligand provides the readout in competition FP. The reaction is depicted schematically in FIG. 2C and had a displacement constant ($K_d$) of 0.4 nM.

TABLE 2

Summary of Data Obtained for gp41 CHR Analogs 3-7, 9 and 10

| Oligomer | gp41-5 Ki (nM)$^a$ | NHR + CHR Tm (° C.)$^b$ | Proteinase K $t_{1/2}$ (min)$^c$ | Cell-Cell Fusion IC50 (nM)$^d$ |
|---|---|---|---|---|
| 3 | 0.2 | 77 | 0.7 | 9 |
| 4 | 3,800 | e | 14 | 390 |
| 5 | 0.2 | 69 | | 7 |
| 6 | 15 | | | |
| 7 | 0.4 | | | |
| 9 | 83 | | | |
| 10 | 9 | 55 | 200 | 5 |

$^a$Dissociation constant ($K_i$) for gp41-5 determined from competition FP experiments.
$^b$Thermal unfolding transition observed by CD at 222 nm for a 1:1 mixture of NHR α-peptide 1 and the indicated CHR analog in PBS at 20 μM total peptide concentration.
$^c$Half-life of a 20 μM solution of peptide in TBS in the presence of 10 μg/mL proteinase K.
$^d$IC$_{50}$ in a cell-based fusion assay.
e. No cooperative thermal transition was observed. --

α-Peptide 3 showed binding affinity for gp41-5 in competition FP experiments (see Table 2) that was below the limit of detection of the assay ($K_i$<0.2 nM). α/β-Peptide analog 4 (SEQ. ID. NO: 4) showed measurable affinity, but it bound the model protein more than 10,000-fold weaker than the prototype α sequence. Unpublished studies of the present inventors suggested that the W—W—I motif found near the N-terminus of 3 is critical for NHR binding. (See also Chan et al. (1998) *Proc. Natl. Acad. Sci. USA* 95:15613-7.) It was thus hypothesized that chimeric derivatives of α/β-peptide 4 which displayed these key hydrophobic side chains on a pure α backbone (i.e., oligomers 5 and 6, SEQ. ID. NOS: 5 and 6, respectively) would show tighter binding to gp41-5. Indeed, (α+α/β)-peptide 5 bound to gp41-5 with sub-nM affinity in the FP assay, indistinguishable from parent α-peptide 3. Extending the α/β segment in 5 toward the N-terminus (α/β-peptide 6) led to a diminution in binding affinity.

One of the fundamental motivations in the sequence-based α→β modification of a biomedically relevant sequence such as the gp41 CHR domain is to create oligomers that mimic the function of the parent α-peptide while displaying enhanced resistance to proteolytic degradation. As shown herein, the ααβααα β backbone confers useful levels of resistance to protease; however, long α-peptide segments in chimeric oligomers are effectively cleaved by proteases.

To generate α/β-peptide analogs of the gp41 CHR domain with β-residues incorporated throughout the sequence, flexible substituted or unsubstituted β²- and/or β³-residues were replaced with cyclically constrained β-residues such as trans-2-aminocyclopentanecarboxylic acid (ACPC) and trans-2-aminopyrrolidinecarboxylic acid APC, see FIG. 1B, and those described in U.S. Pat. Nos. 6,060,585 and 6,613,876, incorporated herein by reference. Ring constraint of the $C_\alpha$-$C_\beta$ bond in a β-amino acid residue restricts torsional freedom, and promotes folding in diverse β-peptides and α/β-peptides. Substitution of three β³-hAla residues in chimeric (α+α/β)-peptide 6 (SEQ. ID. NO: 6) with ACPC generated α/β-peptide 7 (SEQ. ID. NO: 7), which showed a 40-fold improvement in binding to gp41-5 relative to 6. The same β³-hAla→ACPC substitutions were applied to oligomer 4 (SEQ. ID. NO: 4) yielding 9 (SEQ. ID. NO: 9). α/β-Peptide 9 showed a 50-fold higher affinity for gp41-5 than 4. To improve binding further, three β³-hArg residues in 9 were mutated to APC, a cationic analog of ACPC, to produce 10 (SEQ. ID. NO: 10). Gratifyingly, α/β-peptide 10 showed gp41-5 binding affinity ($K_d$=9 nM) that was impressive given its high degree of β-residue content.

α-Peptide 3 has been shown to be a potent inhibitor of HIV-cell fusion in cell culture. In the work described herein, the in vitro results obtained for the best α/β-peptide analog in the competition FP experiments compared favorably to 3. The gp41 CHR mimics were then tested for their ability to block gp41-mediated membrane fusion in a biological milieu. In order to compare the efficacy of α-peptide 3 to select foldamers in a more biologically relevant context, a previously described cell-cell fusion assay was employed. In this experiment, two cell lines are co-cultured. One cell line expresses HIV-1 Env (processed by cellular proteases to generate gp120+gp41) and Tat (an HIV transcriptional activator). The other cell line expresses CD4 (the primary cell surface receptor of HIV) and bears a gene for the enzyme β-galactosidase (β-Gal) preceded by an HIV long terminal repeat sequence (sensitive to activation by Tat). Env-mediated cell-cell fusion leads to expression of β-Gal, which can be quantified by a chemiluminescent enzymatic assay. Compounds 3, 4, 5 and 10 were tested for the ability to disrupt gp41-mediated membrane fusion in the above described assay. The results (Table 2) showed that the best foldamers, compounds 5 and 10 (SEQ. ID. NOS: 5 and 10 respectively), have $IC_{50}$ values that are indistinguishable from α-peptide 3.

The interactions of select α/β-peptides with the gp41 NHR domain were further investigated by circular dichroism (CD) spectroscopy. The CD spectra of 3, 4, 5, 8, 9 and 10 were measured, both alone (see FIG. 5A) and in a 1:1 mixture with NHR α-peptide 1 (see FIGS. 3A, 3B, 3C, and 3D, respectively). See also FIGS. 5B and 5C for the superimposed spectra. The CHR analogs in isolation showed varying degrees of helicity. α-Peptide 3 (FIG. 3A) showed significant helical content at 20 μM in PBS, consistent with earlier published data. α/β-Peptide 10 (FIG. 3D), with seven β³→cyclic-β substitutions, revealed an intense CD minimum, consistent with a well-folded α/β-peptide helix. The observed CD spectrum for each 1:1 mixture of NHR+CHR peptide (FIGS. 3A-3D, solid lines) was compared to that calculated by averaging spectra observed for the corresponding individual oligomers before mixing (FIGS. 3A-3D, dashed lines). α/β-peptides 5 and 10, (SEQ. ID. NOS: 5 and 10, respectively) which showed nM or better affinity for gp41-5 in the competition FP assay, both showed a significant degree of induced helicity when mixed with NHR α-peptide 1. In contrast, α-peptide 3, which had only modest affinity for gp41-5 by FP, showed essentially no cooperative interaction with 1. The magnitude of the CD signatures among the well-folded mixtures (1+3, 1+5 and 1+10, FIGS. 3A, 3C, and 3D, respectively) are similar, but the ratio of intensities at 208 and 222 nm changes as a function of β-residue content (more β-residues tracks with a less intense peak at 222 nm). The well-folded NHRCHR complexes (1+3, 1+5 and 1+10) each showed cooperative thermal transitions (see FIG. 6) with Tp, values that correlate with relative differences in affinity for gp41-5 by competition FP.

It has been shown (data omitted) that mixed α/β backbones (including the ααβααα β pattern employed in the gp41 model) can impart resistance to degradation by proteases, a serious drawback of peptide-based HIV fusion inhibitors. The stability of α-peptide 3 and α/β-peptides 4 and 10 to degradation by the promiscuous serine protease proteinase K was tested. Under the conditions of the proteolysis assay, α-peptide 3 was completely degraded within minutes to yield products resulting from hydrolysis of at least ten different amide bonds in the sequence. α/β-Peptide 4, with simple α→β³ substitution, showed 20-fold improvement in stability relative to prototype α-peptide 3. α/β CHR analog 10 showed an even greater improvement in stability over α-peptide 3 (280-fold). The relative improvement in proteolytic stability of α/β-peptide 10 over 4 likely results from a difference in their inherent helicity, as observed by CD.

The present invention is thus a method employing systematic α→β modifications to yield unnatural α/β polypeptides that retain the biological activity of an α-amino acid prototype, yet resist proteolytic degradation in cell culture and in vivo. As shown in the gp41 model, systematic α→β modifications in the HIV gp41 CHR domain, made in accordance with the present invention leads to α/β-peptide analogs with potent efficacy and enhanced proteolytic stability relative to the original α-peptide. The findings establish the scope of sequence-based backbone modification as a general method to create oligomers that mimic the structure and function of parent α-peptide sequences.

The gp41 model is presented herein as an illustration of how the present invention works in a specific environment. The method can be repeated, using any α-polypeptide as the target or prototype to be mimicked by a corresponding α/β-polypeptide fabricated according to the present method.

Thus, for example, the presently claimed method can be used to fabricate α/β-polypeptides, on a rational basis, to treat rheumatoid arthritis by targeting the interaction between tumor necrosis factor (TNF) and its receptor. See, for example, Williams, Ghrayeb, Feldmann, & Maini (1995) *Immunology* 84:433-439, for a discussion of this protein-protein interaction. Similarly, the presently claimed method can be used to fabricate α/β-polypeptides, on a rational basis, to treat central and peripheral nervous system disorders by targeting the interaction between gallanin and its receptor. See, for example, Mitsukawa, Lu, & Bartfai (2008) *Cell. Mol. Life. Sci.* (June 2008) 65(12):1796-17805 for a discussion regarding gallanin and its receptor and the suitability of using this interaction to design drug targets.

The presently claimed method can also be used to fabricate α/β-polypeptides, on a rational basis, to treat disorders relating to bone and calcium metabolism by targeting the interactions between parathyroid hormone and its receptors (PTH1R and PTH2R). See, for example, Usdin, Bonner, & Hoare (2002), "The parathyroid hormone 2 (PTH2) receptor," *Recept. Channels* 8(3-4):211-218; and Mannstadt, Juppner, & Gardella (1999), "Receptors for PTH and PTHrP: their biological importance and functional properties," *Am. J. Physiol.* 277(5 Pt. 2):F665-675.

The presently claimed method can also be used to fabricate α/β-polypeptides, on a rational basis, to treat disorders relating to serine protease reactions, such as the thrombin reaction. See, for example, EP1141022, which describes a series of α-polypeptide thrombin inhibitors. The present invention can be used to fabricate α/β-polypeptides that adopt similar conformations, have very similar anti-thrombin activity (as demonstrated in the case of the gp41 system), yet have much less susceptibility to proteolytic degradation in cell culture and in vivo.

The presently claimed method can also be used to fabricate α/β-polypeptides, on a rational basis, to inhibit the onset or progression of neoplasms by targeting, for example, the EPH receptors and their ephrin ligands. EPH receptors and their ephrin ligands constitute the largest sub-family of receptor tyrosine kinases (RTKs) and are components of cell signaling pathways involved in animal development. EPH signaling also plays an important role in oncogenic processes observed in several organs. These receptors are involved in a wide range of processes directly related to tumorigenesis and metastasis, including cell attachment and shape, migration, and angiogenesis. Accordingly, EPH expression and signaling activity is a critical system in the tumorigenic process. See, for example, Castano, Davalos, Schwartz & Arango (August 2008) *Histol. Histopathol.* 23(8):1011-1023. Thus, the present method can be used to fabricate α/β-polypeptides, on a rational basis, that mimic ephrin ligands.

Once suitable drug candidates are identified, their biological and/or pharmacological activities may be assayed using any number of well-known and industry-accepted assays.

The anti-inflammatory and immunosuppressive activities of the compounds described herein are determined by means of the following and similar assays: the IL-1β secretion inhibition, LPS fever, cytokine release from THP-1 cells, and functional IL-1 antagonist assays and the assay of carrageenan-induced paw edema in the rat (as described in EP0606044 and EP0618223); the macrophilin binding, Mixed Lymphocyte Reaction (MLR), IL-6 mediated proliferation, localized graft-versus-host (GvH) reaction, kidney allograft reaction in the rat, experimentally induced allergic encephalomyelitis (EAE) in the rat, Freund's adjuvant arthritis, FKBP binding, steroid potentiation and Mip and Mip-like factor inhibition assays (as described in WO9409010, EP0296123 and EP0296122).

The central nervous system (CNS) activity of the compounds described herein is determined by means of the following and similar assays: serotonin ID (5HT 10) receptor agonist assays including the method of Weber et al., *Schmiedeberg's Arch. Pharmacol.* 337, 595-601 (1988), and as described in EP0641787; 5HT 3 receptor agonist assays (as described in GB2240476 and EP0189002); assays for activity in treatment of psychotic disorders and Parkinson's disease, such as the apomorphine-induced gnawing in the rat assay and dopamine receptor (D1 and D2) binding assays (as described in GB20206115 B); assays for dopamine receptor antagonist activity (in relation to schizophrenia and related diseases, as described in EP0483063 and EP0544240); assays for activity in relation to senile dementia and Alzheimer's disease (as described in EP0534904); assays for activity in relation to cerebral ischemia (as described in EP0433239), and assays in relation to gastrointestinal motility such as the peristaltic reflex in isolated guinea pig ileum and assays of anti-serotoninergic effects (specifically at the 5-HT 4 receptors) (as described in EP0505322).

Activity of the compounds described herein in relation to bone and calcium metabolism is determined by assays as (or similar to) those described in WO9402510, GB2218102B and WO8909786.

Activity of the compounds described herein in relation to asthma and other allergic and inflammatory conditions is determined by the following assay procedures: the PDE isoenzyme inhibition, inhibition of eosinophil activation by formyl-Met-Leu-Phe (fMLP), inhibition of TNFα secretion, inhibition of SRS-A production, bacterial endotoxin (LPS)-induced lethality in the guinea pig, arachidonic acid-induced irritant dermatitis in the mouse, relaxation of the human bronchus, suppression of SRS-A-induced bronchoconstriction, suppression of bombesin-induced bronchoconstriction, suppression of methacholine (MeCH)-induced bronchoconstriction in the rhesus monkey and suppression of airways hyperactivity in the guinea pig assays (as described in EP 0664289, WO94/12493 and GB2213482).

The serine protease (e.g., thrombin) inhibition activity of the compounds described herein is determined using assays such as those described in WO9420526. The glycoprotein IIbIIIa antagonist activity of the compounds described herein is determined using the assay procedures described by Cook et al., *Thrombosis and Haemostasis*, 70(3), 531-539 (1993) and *Thrombosis and Haemostasis*, 70(5), 838-847 (1993), and Müller et al. *J. Biol. Chem.*, 268(9), 6800-6808 (1993).

Anticancer activity of the compounds described herein is determined by the anti-tumor activity assay as described in EP0296122 or by trial procedures, for instance as described in GB2239178. Multi-drug resistance (MDR)-reversing activity of the subject compounds is determined by the assays described in EP0296122.

The relevant teachings of the patent documents and other publications referred to above is incorporated herein by reference. Compounds fabricated according to the present invention which have appropriate levels of activity in these assays are useful as pharmaceuticals in relation to the corresponding therapies or disease states.

Thus the invention includes compounds as described herein for use as pharmaceuticals and the use of the compounds for the manufacture of a medicament for the treatment of any disease associated with any of the assays described herein, including infection by the HIV virus. The invention also includes the use of a compound fabricated according to the claimed method as a pharmaceutical, and pharmaceutical compositions comprising an effective amount of such a compound together with a pharmaceutically acceptable diluent or carrier.

The compounds of the invention may be synthesized using solid phase synthesis techniques.

Thus Fmoc-N-Protected β-amino acids can be used to synthesize poly-α/β-peptides by conventional manual solid-phase synthesis procedures under standard conditions on ortho-chloro-trityl chloride resin.

Esterification of Fmoc-β-amino acids with the ortho-chloro-trityl resin can be performed according to the method of Barlos et al., *Tetrahedron Lett.* (1989), 30, 3943. The resin (150 mg, 1.05 mmol Cl) is swelled in 2 ml $CH_2Cl_2$ for 10 min. A solution of the Fmoc-protected β-amino acid in $CH_2Cl_2$ and $iPr_2EtN$ are then added successively and the suspension is mixed under argon for 4 h. Subsequently, the resin is filtered and washed with $CH_2Cl_2$MeOH$iPr_2$EtN (17:2:1, 3×3 min), $CH_2Cl_2$ (3×3 min), DMF (2×3 min), $CH_2Cl_2$ (3×3 min), and MeOH (2×3 min). The substitution of the resin is determined on a 3 mg sample by measuring the absorbance of the dibenzofulvene adduct at 300 nm. The Fmoc group is removed using 20% piperidine in DMF (4 ml, 2×20 min) under Ar bubbling. The resin is then filtered and washed with DMF (6×3 min). For each coupling step, a solution of the β-amino acid (3 equiv.), BOP (3 equiv.) and HOBT (3 equiv.) in DMF (2 ml) and $iPr_2EtN$ (9 eq) are added successively to the resin and the suspension is mixed for 1 h under Ar. Monitoring of the coupling reaction is performed with 2,4,6-trinitrobenzene-sulfonic acid (TNBS) (W. S. Hancock and J. E. Battersby, *Anal. Biochem.* (1976), 71, 260). In the case of a positive TNBS test (indicating incomplete coupling), the suspension is allowed to react for a further 1 h. The resin is then filtered and washed with DMF (3×3 min) prior to the following Fmoc deprotection step. After the removal of the last Fmoc protecting group, the resin is washed with DMF (6×3 min), $CH_2Cl_2$ (3×3 min), $Et_2O$ (3×3 min) and dried under vacuum for 3 h. Finally the peptides are cleaved from the resin using 2% TFA in $CH_2Cl_2$ (2 ml, 5×15 min) under Ar. The solvent is removed and the oily residues are triturated in ether to give the crude α/β-polypeptides. The compounds are further purified by HPLC.

The oral bioavailability of the compounds described herein is determined in the rat using standard procedures. The absolute oral bioavailabilty is expected to be about 1%.

In view of the stable structures which α/β-peptides exhibit in solution, their stability to enzymatic degradation and their encouraging pharmacokinetic properties, the compounds of the invention have the potential to provide useful pharmaceutical products.

As noted above, the gp41 CHR-derived α-peptide, 3 was used as the starting point for α→β modification (FIG. 1A). α-Peptide 3, also known as T-2635, is 50% mutated as compared to the wild type gp41 CHR domain and contains a combination of Xxx→Ala substitutions and engineered i→i+4 salt bridges that were intended to enhance α-helical propensity. α-Peptide 3 represents one of the most successful examples reported to date of improving the antiviral efficacy of gp41 CHR α-peptides via modification of the α-amino acid sequence. The initial studies began with the side chain sequence optimized in 3. Also explored were changes in backbone composition in the form of α→β residue substitution. In α/β-peptide 4, a subset of the α-residues in 3 has been replaced by $β^3$-residues that bear the side chain of the replaced α-residue (see FIG. 1B). Thus, α/β-peptide 4 has the sequence of side chains found in 3 displayed on an unnatural backbone. The $β^3$-residues of 4 are incorporated in an ααβαααβ pattern, which, upon folding, generates a stripe of β-residues that runs along one side of the helix. This design places the β-stripe in 4 distal along the helix circumference to the molecular surface that packs against the gp41 NHR domain trimer in the six-helix bundle.

A competition fluorescence polarization (FP) assay based on a protein model of the gp41 six-helix bundle was used to compare 3 and 4. (See the Examples for details.) The assay measures displacement of a fluorescently-labeled CHR α-peptide from an engineered five-helix bundle protein, gp41-5, which contains three NHR segments and two CHR segments. Affinity for the gp41-5 protein construct correlates with the ability of CHR-mimetic agents to bind to the gp41 pre-hairpin intermediate formed just prior to HIV-cell fusion. As expected, α-peptide 3 binds very tightly to gp41-5 ($K_i$<0.2 nM; Table 1). The analogous α/β-peptide 4, however, displays only weak affinity for gp41-5, >10,000-fold lower than that of 3. The modest potency of α/β-peptide 4 in this protein-based assay is comparable to that displayed by a number of small molecules and peptidomimetics in comparable experiments.

In an effort to understand the dramatic differences in binding between 3 and 4 and to improve the affinity of the α/β-peptide for gp41, chimeric α/β-peptides 5 and 6 were prepared and characterized. Both 5 and 6 contain a pure α segment at the N-terminus and an α/β segment at the C-terminus; these oligomers are chimeras of α-peptide 3 and α/β-peptide 4. α/β-Peptide 5 displays very high affinity for gp41-5, indistinguishable from that of α-peptide 3; however, extending the α/β segment toward the N-terminus (as in 6) causes a significant loss of affinity. The sensitivity of the N-terminal segment to α→$\beta^3$ modification is consistent with data showing that side chains in this region, especially those corresponding to $Trp_3$, $Trp_6$ and $Ile_{10}$ in 3, play a crucial role in CHR binding to the NHR trimer. (29)

α/β-Peptides 5 and 6 represent an improvement in gp41 mimicry relative to 4, but it would be desirable to place β-residues throughout an α/β-peptide sequence in order to maximize resistance to proteolysis. Each α→$\beta^3$ replacement, however, adds a flexible bond to the backbone, which should increase the conformational entropy penalty associated with helix formation. The greater conformational entropy of the unfolded state of 4 relative to 3, arising from eleven α→$\beta^3$ replacements, may account for the large difference in binding affinity for gp41-5 between these two oligomers. Although β-residues are the source of this loss of stability, these residues provide an avenue for conformational pre-organization that is made uniquely possible by their chemical structure. Incorporation of cyclic β-residues (e.g., ACPC and APC, FIG. 1B) can constrain the $C_\alpha$-$C_\beta$ backbone torsion and thereby enhance folding propensity without disrupting backbone amide hydrogen bonding.

The impact of conformational preorganization in the context of gp41 mimicry was probed by replacing a subset of $\beta^3$-residues with cyclic analogues. The first comparison involved α/β-peptide 7, the analogue of 6 in which the three $\beta^3$-hAla residues are replaced by ACPC (FIGS. 1A and 1B). Both $\beta^3$-hAla and ACPC are non-polar, and this similarity was expected to maintain the physical properties that emerge from side chain sequence. The >30-fold higher affinity for gp41-5 displayed by 7 relative to 6 supports the hypothesis that residue-based rigidification is a useful complement to sequence-based design for developing peptide-mimetic foldamers. Replacement of two $\beta^3$-hArg residues in oligomer 7 with APC, a heterocyclic analogue of ACPC, leads to α/β-peptide 8, which showed a very high affinity for gp41-5. $APC_{36}$ in α/β-peptide 8 is in a region of the CHR sequence that does not engage the NHR region contained in gp41-5; this observation may explain the similar $K_i$ values of 7 and 8. Additional evidence of the favorable contribution of cyclic β-residues comes from comparison of oligomers 4, 9 and 10, each of which has β-residues throughout the sequence. α/β-Peptide 9 was generated from 4 by four $\beta^3$-hAla→ACPC replacements, which leads to a >45-fold improvement in $K_i$. Replacement of the three $\beta^3$-hArg residues of 9 with APC, to generate 10, improves $K_i$ by a further ~10-fold. Relative to completely flexible α/β-peptide 4, rigidified analogue 10 ($K_i$=9 nM) shows ~380-fold enhanced binding to gp41-5.

The interactions of CHR α-peptide 3 and α/β-peptide analogues 4, 5, 8 and 10 with a peptide derived from the gp41 NHR domain (1) were investigated by circular dichroism (CD) spectroscopy. NHR α-peptide 1 forms a six-helix bundle when mixed with gp41 CHR α-peptides; this six-helix bundle is thought to represent the post-fusion state adopted by gp41 in the course of viral entry. α-Peptide 3 showed significant helical content at 20 μM in PBS, consistent with previously published data (FIG. 5A). α/β-Peptide 4 showed no significant helicity under similar conditions; however, analogue 10, with seven $\beta^3$→cyclic-β substitutions, showed an intense CD minimum, consistent with a well-folded α/β-peptide helix (FIG. 5A). The observed CD spectrum for each 1:1 mixture of NHR+CHR peptide was compared (FIGS. 3A through 3D, and 5B, solid lines) to that calculated by averaging spectra for the corresponding individual oligomers (FIGS. 3A through 3D and 5B, dashed lines). α/β-Peptides 5, 8 and 10, which displayed high affinity for gp41-5 in the competition FP assay, each showed a significant degree of induced helicity when mixed with NHR α-peptide 1, which is consistent with six-helix bundle formation. By contrast, α/β-peptide 4, which has only modest affinity for gp41-5, showed essentially no interaction with 1. The magnitude of the CD signatures among the well-folded mixtures (1+3, 1+5, 1+8 and 1+10) are similar, but the ratio of intensities at 208 and 222 nm changes as a function of β-residue content (higher β-residue content is correlated with a less intense peak at 222 nm). This trend is consistent with previous studies on helical oligomers containing mixed α/β backbones. The complexes formed by 1+3, 1+5, 1+8 and 1+10 each showed highly cooperative thermal transitions (FIG. 5C). The trend in $T_{m,app}$ values (i.e., apparent $T_m$) correlates with differences in affinity among 3, 5, 8 and 10 for gp41-5 in the competition FP assay; that is, stronger binding to gp41-5 correlates with more stable assembly with NHR peptide 1.

Crystal Structures.

X-ray crystallography was employed to compare the heteromeric six-helix bundles formed by NHR α-peptide 1 with CHR α-peptide 3, chimeric CHR α/β-peptide 8 or CHR α/β-peptide 10 (see Table 3).

TABLE 3

X-ray data collection and refinement statistics

|  | 1 + 3 complex | 10 | 1 + 10 complex | 1 + 8 complex |
|---|---|---|---|---|
| Data collection |  |  |  |  |
| Space group | $P2_12_12$ | C2 | $P4_132$ | H32 |
| Cell dimensions |  |  |  |  |
| a, b, c (Å) | 37.6, 179.0, 33.1 | 71.3, 44.0, 58.1 | 84.9, 84.9, 84.9 | 57.0, 57.0, 186.3 |
| α, β, γ (°) | 90, 90, 90 | 90, 105.4, 90 | 90, 90, 90 | 90, 90, 120 |
| Resolution (Å) | 44.8-2.0 (2.1-2.0)* | 50.0-2.1 (2.18-2.10)* | 50.0-2.8 (2.9-2.8)* | 50.0-2.8 (2.9-2.8)* |
| $R_{sym}$ (%) | 5.0 (26.2) | 6.7 (35.6) | 6.1 (51.2) | 5.8 (38.8) |
| I/σI | 28.0 (4.7) | 16.1 (3.5) | 31.6 (2.8) | 16.8 (3.7) |
| Completeness (%) | 99.9 (100) | 99.8 (99.8) | 99.8 (98.2) | 99.5 (100) |
| Redundancy | 8.6 (3.6) | 3.5 (3.4) | 7.8 (6.2) | 5.9 (6.2) |
| Refinement |  |  |  |  |
| Resolution (Å) | 25.0-2.0 | 25.0-2.1 | 25.0-2.8 | 25.0-2.8 |
| No. reflections | 15,123 | 9,769 | 2,730 | 2,947 |
| $R_{work}/R_{free}$ (%) | 20.9/26.0 | 20.4/24.9 | 26.6/30.7 | 25.2/31.1 |
| Avg. B factor (Å$^2$) |  |  |  |  |
| RMSD |  |  |  |  |
| Bond lengths (Å) | 0.013 | 0.015 | 0.013 | 0.018 |
| Bond angles (°) | 1.1 | 2.0 | 1.7 | 1.8 |

*Highest resolution shell is shown in parenthesis.

Although the mutations to the native CHR sequence that lead to α-peptide 3 were not intended to modify the nature of its binding interactions with the gp41 NHR domain, direct evidence was sought that the six-helix bundle structure was unchanged relative to that formed by 1 and the native CHR sequence. A co-crystal of α-peptides 1 and 3 was obtained and its structure solved to 2.0 Å resolution. See FIG. 4A. The resulting six-helix bundle is essentially identical to that for 1+2 (see FIG. 4B) which contains the native CHR sequence; the root mean square deviation (rmsd) is 0.73 Å for $C_\alpha$ atoms.

A crystal of the 1+10 complex was also obtained and its structure solved to 2.8 Å resolution. See FIG. 4D. α-Peptide 1 and α/β-peptide 10 combine to form a six-helix bundle that is similar to the assembly formed by 1+3 (duplicated in FIG. 4C to allow a side-by-side comparison). A crystal containing only α/β-peptide 10 (not shown) was obtained as well. The structure of 10 alone, solved to 2.1 Å resolution, revealed a parallel trimeric helix bundle with a hydrophobic core comprising the residues that engage the gp41 NHR trimer in the six-helix bundle formed by 1+10. The self-assembly of cup-peptide 10 in the crystalline state parallels the behavior previously observed for prototype α-peptide 3, which was shown to self-assemble in solution.

The core NHR trimers in the structures of 1+10 and 1+3 are highly homologous (0.65 Å $C_\alpha$ rmsd for NHR residues 3-30). When the two bundles are aligned via the NHR trimer, the CHR helices track very closely in the C-terminal segment (0.84 Å $C_\alpha$ rmsd for residues 16-33) but diverge near the N-terminus (4.2 Å $C_\alpha$ rmsd for residues 2-15). This divergence reflects a greater superhelical twist in α-peptide 3 relative to α/β-peptide 10. The divergent portion of the helix formed by 10 contains the two Trp residues that, in CHR α-peptides, are essential for stable six-helix bundle formation. In the structure of 1+10, the side chains of $Trp_3$ and $Trp_5$ were not resolved in electron density, suggesting a high degree of disorder. In addition, significant disorder was observed in the side chains of NHR residues $Lys_{29}$ and $Trp_{26}$, which pack around CHR $Trp_5$ in the 1+3 complex. FIGS. 4F and 4G depict overlays of the all-α-peptide helix bundle-formed 1+3 with that formed by 1+10 (FIG. 4F) and 1+8 (FIG. 4G).

Given the well-established role of the gp41 CHR domain Trp-Trp-Ile motif in six-helix bundle formation, the observation that the N-terminal segment of α/β-peptide 10 does not engage the NHR binding pocket in the crystal structure of the 1+10 complex is intriguing. Removal of the first ten residues of α/β-peptide 10 leads to oligomer 11, in which the Trp-Trp-Ile motif is not present (see FIG. 1A). If the N-terminal region of 10 were not involved in binding to the NHR trimer in solution, as might be suspected based on the crystal structure of 1+10, then 11 should show affinity for gp41-5 that is comparable to that of 10. However, α/β-peptide 11 showed no measurable affinity for gp41-5 ($K_i$>10 μM), indicating that the N-terminal segment of 10 is essential for high-affinity binding to gp41-5 in solution.

Motivated by the differences between the CHR domain N-terminal segments in the 1+3 complex and the 1+10 complex, the structure of NHR peptide 1 in complex with CHR α/β-peptide 8, a chimera of α-peptide 3 and α/β-peptide 10, was investigated. The 1+8 complex was crystallized and its structure solved to 2.8 Å resolution. See FIG. 4E. Relative to α/β-peptide 10, chimeric α/β-peptide 8 tracks much more closely with the CHR helix (3) in the all-α-peptide, six-helix bundle formed by 1+3 (FIG. 4C, 1.4 Å $C_\alpha$ rmsd for residues 2-33). The side chains of the Trp-Trp-Ile motif in the N-terminal segment of 8 show the expected packing into the binding pocket on the NHR core trimer (data not shown). Based on this result and the behavior of truncated α/β-peptide 11, it is suspected that the lack of direct contact between the N-terminal portion of 10 and the NHR trimer in the 1+10 complex is an artifact of crystal packing.

Antiviral Activity.

Two sets of experiments were performed to evaluate the activities of α-peptide 3 and α/β-peptides 4, 5 and 10 in a biological context. The first experiment compared the oligomers in a cell-cell fusion assay based on expression of the env gene of the HIV-1 clone HxB2, an assay that is commonly used to model gp41-mediated HIV-cell fusion. (Deng Y Q, Zheng Q, Ketas T J, Moore J P, & Lu M (2007) Protein design of a bacterially expressed HIV-1 gp41 fusion inhibitor. *Biochemistry* 46(14):4360-4369.) The cell-cell fusion assay results (Table 4) showed that α/β-peptides 5 and 10 have $IC_{50}$ values indistinguishable from that of α-peptide 3, while α/β-peptide 4 is much less effective. Compounds 3, 4, 5 and 10 were then evaluated for the ability to prevent HIV infection of the cell line TZM-bl. (Wei X P, et al. (2002) Emergence of resistant human immunodeficiency virus type 1 in patients receiving fusion inhibitor (T-20) monotherapy. *Antimicrob Agents Chemother* 46(6):1896-1905.) These studies employed one T-cell line adapted strain and three primary isolates; two of the strains are X4-tropic, and the other two are R5-tropic.

TABLE 4

Summary of physical and functional data obtained for gp41 CHR analogues 3-11.

| Oligomer | gp41-5 binding affinity by FP [a] $K_i$ (nM) | NHR + CHR stability by CD [b] $T_{m, app}$ (° C.) | Stability to Proteinase K [c] $t_{1/2}$ (min.) | Cell-cell fusion inhibition [d] $IC_{50}$ (nM) | Inhibition HIV-1 infectivity, $IC_{50}$ (nM) [e] | | | |
|---|---|---|---|---|---|---|---|---|
| | | | | | X4 strains | | R5 strains | |
| | | | | | NL4-3 | HC4 | CC 1/85 | DJ258 |
| 3 | <0.2 | 77 | 0.7 | 9 ± 3 | 5 ± 0.6 | 27 ± 4 | 140 ± 20 | 58 ± 6 |
| 4 | 3,800 | —[f] | 14 | 390 ± 40 | 700 ± 60 | 590 ± 100 | 1300 ± 100 | 960 ± 200 |
| 5 | <0.2 | 67 | | 7 ± 2 | 10 ± 2 | 55 ± 8 | 270 ± 20 | 280 ± 90 |
| 6 | 15 | | | | | | | |
| 7 | 0.4 | | | | | | | |
| 8 | 0.3 | 65 | | | | | | |
| 9 | 83 | | | | | | | |
| 10 | 9 | 55 | 200 | 5 ± 2 | 28 ± 3 | 59 ± 10 | 180 ± 30 | 110 ± 40 |
| 11 | >10,000 | | | | | | | |
| T-20 | | | | | 700 ± 100 | 250 ± 20 | 1400 ± 400 | 330 ± 60 |

[a] Dissociation constant ($K_i$) for binding to the protein gp41-5 as determined by competition FP experiments.
[b] Melting temperature ($T_{m, app}$) for the thermal unfolding transition observed by CD at 222 nm for a 1:1 mixture of NHR α-peptide 1 and the indicated CHR analogue at 20 μM total peptide concentration in PBS.
[c] Half-life ($t_{1/2}$) of a 20 μM solution of peptide in TBS in the presence of 10 μg/mL proteinase K.
[d] Values are the means ± S.E.M. of $IC_{50}$ values obtained in three independent experiments. The envelope protein expressed was of the HxB2 clone, derived from the T-cell-line-adapted isolate IIIB of clade B.
[e] Values are the means ± S.E.M. of $IC_{50}$ values obtained in three independent experiments.
[f] The temperature dependent CD for the 1 + 4 mixture was not significantly different than that calculated from the average of the temperature dependent CD spectra of 1 alone and 4 alone.

The results of the infectivity assays (Table 4, FIGS. 10A, 10B, 10C, and 10D) show similar biological potencies among 3, 5 and 10 for HIV-1 strains that use different co-receptors. This finding indicates the blocking of a necessary, shared step in entry through peptide interactions with conserved regions of gp41. It may be noted that there is imperfect correlation between $K_i$ for binding to gp41-5 and $IC_{50}$ values in cell-based assays among the compounds reported here. For example, the affinity of 10 for gp41-5 was >45-fold higher than that of 5, yet $IC_{50}$ values for 10 were sometimes lower than for 5. There are several possible reasons for this discrepancy. Sequence differences between the CHR and NHR domains found in gp41-5 and those found in the viruses tested may lead to better correlation between gp41-5 binding affinity and antiviral activity against some strains relative to others. In addition, it has previously been suggested that the association rates for CHR peptides binding to gp41 are a better predictor of relative antiviral potencies than are equilibrium binding affinities. (Steger H K & Root M J (2006) Kinetic dependence to HIV-1 entry inhibition. *J Biol Chem* 281(35):25813-25821.) The rigidified backbone in 10 may alter its association rate with gp41 relative to that of 5. Sensitivity to gp41-derived fusion inhibitors may be affected by many factors that differ among strains of virus, including the amount of Env incorporated into the virion, the strength of Env interactions with CD4 and with co-receptors, the kinetics and energetics of the fusion process, as well as amino acid variation in the binding site for inhibitory peptides. Overall, the antiviral assays results strongly support the hypothesis that CHR-derived α/β-peptides effectively mimic gp41 in a complex biological milieu.

Proteolytic Susceptibility.

An important motivation for developing foldamer antagonists of protein-protein interactions is the prospect of diminishing sensitivity to proteolytic degradation. Rapid destruction by proteolytic enzymes represents a significant drawback to the clinical use of α-peptide drugs. The susceptibilities of α-peptide 3 and α/β-peptides 4 and 10 to degradation by proteinase K, a promiscuous serine protease, were compared. Under the assay conditions, α-peptide 3 was completely degraded within minutes (FIG. 9A); mass spectrometry revealed hydrolysis of at least ten different amide bonds in the sequence (FIG. 9D, top sequence). α/β-Peptide 4, with exclusively α→$β^3$ substitution, showed 20-fold improvement in stability relative to prototype α-peptide 3. See FIG. 9B and FIG. 9D, middle sequence. Rigidified α/β-peptide 10 showed an even greater improvement in stability over α-peptide 3 (280-fold). See FIG. 9C and FIG. 9D, bottom sequence. The greater stability of α/β-peptide 10 relative to α/β-peptide 4 likely results from the greater helical propensity of 10, as detected by CD. The small number of proteolysis products observed for α/β-peptide 10 by mass spectrometry (FIG. 9D) supports previous observations that β-residues in mixed α/β backbones tend to protect neighboring amides from proteolytic cleavage.

Many proteins display surfaces that participate in highly selective interactions. Information flow mediated by protein-protein interactions is essential for normal function of individual cells and entire organisms; such interactions can play key roles in disease as well. There is considerable motivation to identify strategies for inhibiting the formation of specific inter-protein complexes. At the clinical level, the most successful approach to this goal involves the use of engineered proteins or protein fragments, i.e., molecules constructed from the same building blocks as the protein targets themselves. The motivating hypothesis of the presently claimed method is that recognition surfaces displayed by proteins can be mimicked with unnatural oligomers that adopt protein-like conformations and display protein-like side chains, and that such oligomers will function as inhibitors of natural protein-protein associations. Natural protein sequences are logical starting points for designing folded oligomers with nonnatural backbones that have sophisticated functions. The data presented here provide strong support for these hypotheses in the context of a widely studied viral infection process.

The results presented herein indicate that a long α-helical segment, the CHR region of HIV protein gp41, can be structurally and functionally mimicked by oligomers composed of α- and β-amino acid residues. A two-stage process was required to generate an α/β-peptide that manifests a favorable profile of properties, including strong association with the intended binding partner, potent inhibition of HIV infection in a cell-based assay and resistance to proteolytic cleavage. The first design stage involves replacement of selected α-residues in a parent peptide sequence with homologous β-residues that retain the original side chains. The second design stage involves selective replacement of flexible $β^3$-residues with cyclically preorganized β-residues. These modifications are intended to remove deleterious backbone flexibility that is unavoidably introduced with the initial α→$β^3$ modifications.

Using a two-stage approach for creation of an effective α/β-peptide mimic of the gp41 CHR segment is noteworthy in light of our previous findings in a different and inherently simpler protein recognition system. Mimicry of BH3 domains, short α-helical segments that mediate protein-protein interactions in the Bcl-2 protein family, required only the first stage of this design approach, simple α→$β^3$ substitution throughout the prototype sequence. (Home W S, Boersma M D, Windsor M A, & Gellman S H (2008) Sequence-based design of α/β-peptide foldamers that mimic BH3 domains. *Angew Chem Int Ed* 47(15):2853-2856.) In contrast, α/β-peptide 4, which showed only modest affinity for gp41-5, was the most potent gp41 mimic identified among a series of α/β-peptides designed by exploring alternative α/$β^3$ backbone patterns in the native gp41 CHR domain and related sequences.

The results reported here represent a substantial advance relative to earlier efforts to develop unnatural oligomers that mimic α-helices involved in protein-protein recognition events. Previous work has been limited to relatively short α-helical targets, typically only two to four helical turns. Efficacies of oligomers developed in these prior studies have generally been modest ($IC_{50}$ values greater than 1 μM). Moreover, in most previously studied systems, effective inhibition has been possible with small molecule antagonists. The present results are distinctive because the data show that a long α-helix (~10 turns) can be structurally and functionally mimicked with a rationally designed oligomer. To date, efforts to disrupt gp41 six-helix bundle assembly with small molecules have been relatively unsuccessful.

The present work demonstrates the value of designing unnatural oligomers that can "read" the sophisticated recognition signals that have been evolutionarily encoded in natural proteins. Potent inhibition of HIV infectivity by α/β-peptides is an important advance in the development of functional foldamers.

EXAMPLES

Reagents: Protected α-amino acids and resins used in peptide synthesis were purchased from Novabiochem (a wholly owned subsidiary of EMD Chemicals Inc. and Merck KGaA, Darmstadt, Germany). Protected $β^3$-amino acids were purchased from PepTech (Burlington, Mass., USA). Cyclically constrained β-residues, Fmoc-ACPC and Fmoc-APC(Boc), were prepared as previously described. Lee, LePlae, Porter, and Gellman, *J. Org. Chem.* 2001, 66, 3597-3599; LePlae, Umezawa, Lee, and Gellman, *J. Org. Chem.* 2001, 66, 5629-5632. 2-(1H-Benzotriazole-1-yl)-1,1,3,3-tetramethylaminium hexafluoro-phosphate (HBTU) was purchased from AnaSpec (San Jose, Calif., USA). 5-Carboxyfluorescein was purchased from Invitrogen (Carlsbad, Calif., USA). 1-Methyl-2-pyrollidinone (NMP) was purchased from Advanced Chemtech (Louisville, Ky., USA). All other reagents were purchased from Sigma-Aldrich Corp. (St. Louis, Mo., USA) or Fisher Scientific (Pittsburgh, Pa., USA) and used as received.

Synthesis:

All peptides were prepared on "NovaSyn TGR"-brand resin (Novabiochem). α-Peptides were prepared by standard Fmoc solid phase peptide synthesis methods on a Symphony Multiple Peptide Synthesizer (Protein Technologies, Inc., Tucson, Ariz., USA). α/β-Peptides were prepared by automated Fmoc solid phase peptide synthesis on a Synergy 432A automated synthesizer (Applied Biosystems, Foster City, Calif., USA). α/β-Peptides were also prepared manually by microwave-assisted Fmoc solid phase peptide synthesis. Erdelyi and Gogoll (2002) *Synthesis* 11:1592-1596. The N-terminus of each peptide was capped by treatment with 8:2:1 DMF/DIEA/Ac$_2$O. The resin was washed thoroughly (3×DMF, 3×CH$_2$Cl$_2$, 3×MeOH) and then dried under vacuum. All peptides were cleaved from resin by treatment with 94:2.5:2.5:1 TFA/H$_2$O/ethanedithiol/triisopropylsilane. The resin was filtered, washed with additional TFA, and the combined filtrates concentrated to 2 mL under a stream of dry nitrogen. Crude peptide was precipitated from the cleavage mixture by addition of cold ether (45 mL). The mixture was centrifuged, decanted, and the remaining solid dried under a stream of nitrogen. Peptides were purified by reverse phase HPLC on a prep-C$_{18}$ column using gradients between 0.1% TFA in water and 0.1% TFA in acetonitrile. The identity and purity of the final products were confirmed by MALDI-TOF-MS and analytical HPLC, respectively. Stock solution concentrations were determined by UV absorbance. Gill, S. C.; Vonhippel, P. H. *Anal. Biochem.* 1989, 182, 319-326. MALDI-TOF-MS (monoisotopic [M+H]$^+$, m/z): 1: obsd.=4162.6, calc.=4162.4; 2: obsd.=4288.7, calc.=4288.0; 3: obsd.=4455.0, calc.=4455.3; 4: obsd.=4609.9, calc.=4609.5; 5: obsd.=4526.1, calc.=4525.4; 6: obsd.=4552.7, calc.=4553.4; 7: obsd.=4631.6, calc.=4631.4; 8: obsd.=4516.5, calc.=4515.3; 9: obsd.=4713.0, calc.=4713.5; 10: obsd.=4539.9, calc.=4539.4; 11: obsd.=3299.4, calc.=3299.8.

Synthesis of Flu-C38:

"NovaSyn TGR"-brand resin bearing the full-length C38 peptide with free N-terminus (WMEWDREINNYTSLIH-SLIEESQNQQEKNEQELLELDK; SEQ. ID. NO: 23) was prepared on a 25 µmol scale by standard Fmoc solid phase peptide synthesis methods on a Symphony Multiple Peptide Synthesizer (Protein Technologies, Inc.). Following synthesis, the resin was transferred to a fritted syringe. 5-Carboxyfluorescein (28 mg, 0.075 mmol) and HOBT.H$_2$O (11 mg, 0.075 mmol) were dissolved in N-methyl-2-pyrrolidinone (0.75 mL). Diisopropylcarbodiimide (12 µL, 0.075 mmol) was added. The resulting solution was transferred to the peptide-bearing resin. The reaction vessel was covered in foil and placed on a shaker overnight. The resin was washed with DMF (3×), and the coupling reaction was repeated with fresh reagents. The resin was then washed with DMF (3×), 20% piperidine (2×), DMF (3×), CH$_2$Cl$_2$ (3×), and MeOH (3×). Fischer, R.; Mader, O.; Jung, G.; Brock, R. *Bioconjugate Chem.* 2003, 14, 653-660. The crude peptide was cleaved and purified as described above. Stock solutions, prepared in water, were quantified by visible absorbance ($\epsilon_{494}$=68,000 M$^{-1}$ cm$^{-1}$ at pH 8). MALDI-TOF-MS (monoisotopic [M+H]$^+$, m/z): obsd.=5089.3, calc.=5089.3.

Crystallization.

Hanging drops were prepared by mixing 1 µL of crystallization stock and 1 µL of reservoir buffer followed by room temperature equilibration over 0.7 mL buffer. Stock solutions of the 1+3 and 1+8 complexes were prepared by mixing concentrated stocks of the individual peptides in a 1:1 ratio to a final concentration of 2.2 mM total peptide in water. Crystals of 1+3 were obtained from a reservoir buffer comprising 0.1 M Tris pH 8.5, 1 M (NH$_4$)H$_2$PO$_4$. Crystals of the 1+8 complex were grown a reservoir buffer comprising 0.4 M Li$_2$SO$_4$H$_2$O, 12% v/v PEG 8000, 20% v/v glycerol. In initial attempts to crystallize the 1+10 complex, a stock solution was prepared by mixing concentrated stocks of the individual peptides in a 1:1 ratio to a final concentration of 0.76 mM total peptide in water. Stocks of 1+10 prepared in this way were not fully soluble. However, the resulting viscous suspension yielded crystals of α/β-peptide 10 alone from a well buffer comprised of 0.5 M ammonium sulfate, 0.1 M HEPES-Na, pH 7.5, 30% v/v 2-methyl-2,4-pentanediol. For subsequent crystallization trials of 1+10, the stock solution of the complex was prepared by refolding the 1:1 peptide mixture at 130 µM total peptide in water followed by concentration to ~1.1 mM by centrifugation at 4° C. through a 10 kDa molecular weight cutoff membrane. Crystals of 1+10 were obtained from a stock prepared in this way and a reservoir buffer comprised of 0.2 M NaCl, 0.1 M Tris pH 8.5, 25% wv PEG 3350.

X-Ray Data Collection, and Structure Determination.

All crystals were flash frozen in liquid nitrogen. Crystals of the 1+3 complex were briefly soaked in 0.08 M Tris pH 8.5, 1.6 M (NH$_4$)H$_2$PO$_4$, 20% v/v glycerol prior to freezing. Crystals of 10 and 1+8 were frozen directly from the crystallization drop. Crystals of the 1+10 complex were soaked briefly in 0.2 M NaCl, 0.1 M Tris pH 8.5, 25% wv PEG 3350, 20% v/v glycerol prior to freezing. Diffraction data for the 1+3 and 1+8 complexes were collected on a Bruker X8 Proteum Diffractometer (Bruker AXS, Inc. Madison, Wis. USA) using Cu K$_\alpha$ radiation and were processed with the Bruker Proteum2 software package. Diffraction data for the crystals of 10 and the 1+10 complex were collected at the Life Sciences Collaborative Access Team beamline 21-ID-G at the Advanced Photon Source, Argonne National Laboratory, and were processed with HKL-2000-brand software (HKL Research, Inc., Charlottesville, Va., USA). Structure determination was carried out using the CCP4 software suite. Collaborative Computational Project Number 4 (1994) The CCP4 Suite—Programs for Protein Crystallography. *Acta Crystallogr, Sect D* 50:760-763. Molecular replacement was carried out with Phaser software (McCoy A J, Grosse-Kunstleve R W, Storoni L C, & Read R J (2005) Likelihood-enhanced fast translation functions. *Acta Crystallogr, Sect D* 61:458-464) or Molrep software (Vagin A & Teplyakov A (1997) MOLREP: An automated program for molecular replacement. *J Appl Crystallogr* 30(6):1022-1025). Refinement was accomplished by a combination of Refmac (Murshudov G N, Vagin A A, & Dodson E J (1997) Refinement of macromolecular structures by the maximum-likelihood method. *Acta Crystallogr, Sect D* 53:240-255) for automated refinement, Coot (Emsley P & Cowtan K (2004) Coot: Model-building tools for molecular graphics. *Acta Crystallogr, Sect D* 60:2126-2132) for manual model building, and ARP/wARP for automated water building and free atom density modification. (Lamzin V S & Wilson K S (1993) Automated refinement of protein models. *Acta Crystallogr, Sect D* 49:129-147.) The structure of the 1+3 complex was solved using a search model derived from a published gp41 hexamer structure (PDB ID: 1AIK). Chan D C, Fass D, Berger J M, & Kim P S (1997) Core structure of gp41 from the HIV envelope glycoprotein. *Cell* 89(2):263-273. The structure of α/β-peptide 10 was solved using a CHR helix from the 1+3 complex as a search model. The structure of the 1+10 complex was solved using two search models, an NHR helix from the 1+3 complex and a CHR helix from the structure of α/β-peptide 10 alone. The structure of the 1+8 complex was solved using two search models, an NHR helix from the 1+3 complex and a chimeric CHR helix prepared from the structures of 1+3 and 1+10. Molecular graphics were prepared using PyMOL (DeLano Scientific, Palo Alto, Calif., USA).

Protease Stability.

Stock solutions of peptides were prepared at a concentration of 25 µM (based on UV absorbance) in TBS. A solution of proteinase K was prepared at a concentration of 50 µg/mL (based on weight to volume) in TBS. For each proteolysis reaction, 40 µL of peptide stock was mixed with 10 µL of proteinase K stock. The reaction was allowed to proceed at room temperature and quenched at the desired time point by addition of 100 µL of 1% TFA in water. 125 µL of the resulting quenched reaction was injected onto an analytical reverse phase HPLC and run on a gradient between 0.1% TFA in water and 0.1% TFA in acetonitrile. The amount of starting peptide present quantified by integration of the peak at 220 nm. Duplicate reactions were run for each time point. Half-lives were determined by fitting time dependent peptide concentration to an exponential decay using GraphPad Prism-brand software (GraphPad Software, Inc., La Jolla, Calif., USA). Crude samples for some time points were analyzed by MALDI-MS, and the products observed were used to identify amide bonds cleaved in the course of the reaction.

Expression, Purification, and Refolding of gp41-5.

The sequence of the gp41-5 construct used herein is below.

(SEQ. ID. NO: 24)
MSGIVQQQNNLLRAIEAQQHLLQLTVWGIKQLQARILSGGSGGWMEWDR

EINNYTSLIHSLIEESQNQQEKNEQELLGGSGGSGIVQQQNNLLRAIEA

QQHLLQLTVWGIKQLQARILSGGSGGWMEWDREINNYTSLIHSLIEESQ

NQQEKNEQELLGGSGGSGIVQQQNNLLRAIEAQQHLLQLTVWGIKQLQA

RIL

Expression, purification, and refolding of gp41-5 were carried out as previously described. Frey, G.; Rits-Volloch, S.; Zhang, X. Q.; Schooley, R. T.; Chen, B.; Harrison, S. C. *Proc. Natl. Acad. Sci. U.S.A.* 2006, 103, 13938-13943. A sample of the gp41-5 plasmid, provided by Prof. Stephen Harrison (Harvard University), was transfected into *E. coli* cells (Rosetta™ strain, Novagen) by electroporation. A single colony was grown overnight in 20 mL LB supplemented with 50 µg/mL ampicillin (resistance provided by the gp41-5 plasmid) and 30 µg/mL chloramphenicol (resistance provided by the plasmid for rare tRNAs included in the Rosetta™ strain). 500 mL of antibiotic supplemented LB was inoculated with 5 mL of the overnight starter culture. Cells were grown at 37° C. to an $OD_{600}$ of 0.75 and subsequently induced by addition of IPTG to a final concentration of 1 mM. The cells were grown for an additional 3 hr at 37° C., and then centrifuged at 12,000 g for 15 min at 4° C. The cell pellet was dissolved in ice cold glacial acetic acid and left on ice for 45 min with periodic agitation. The suspension was centrifuged at 39,000 g for 15 min at 4° C. The supernatant was decanted and lyophilized. The crude protein was purified by preparative HPLC on a $C_{18}$ column eluted by a gradient between 0.1% TFA in water and 0.1% TFA in acetonitrile. Purified protein was lyophilized and stored at −40° C. until refolding. For refolding, purified gp41-5 (~2 mg) was dissolved in 10 mL of 6 M guanidinium chloride. The resulting solution was dialyzed at room temperature against 0.1 M glycine pH 3.6 (1×) followed by PBS (2×). Precipitate was removed by centrifugation and the resulting protein used without further purification.

Fluorescence Polarization.

Fluorescence polarization assays were conducted at room temperature in black polystyrene plates. All measurements were performed in duplicate wells. The assay buffer was composed of 20 mM phosphate, pH 7.4, 1 mM EDTA, 50 mM NaCl, 0.2 mM $NaN_3$, 0.5 mg/mL "Pluronic F-68"-brand polyoxyalkylene ether surfactant. The binding affinity of Flu-C38 for gp41-5 was measured by titrating a fixed concentration of the labeled peptide (0.2 nM) with increasing concentrations of protein in 384-well plates with a final volume of 50 µL per well in assay buffer with 1% v/v DMSO (added to mimic the conditions of the competition FP experiments). All wells were run in duplicate. The plate was allowed to equilibrate for 30 min and analyzed on an Envision 2100 plate reader. The data were fit using Graphpad Prism software (Graphpad Software Inc., La Jolla, Calif.) to a FP direct-binding model. Roehrl, M. H. A.; Wang, J. Y.; Wagner, G. *Biochemistry* 2004, 43, 16056-16066. The $K_d$ of the tracer was determined to be 0.4±0.1 nM. The binding affinity measured is somewhat tighter than that previously reported for the gp41-5/Flu-CHR interaction ($K_d$=3 nM), but the previous study utilized a much higher concentration of tracer in the direct binding experiment (5 nM). The lower limit of a $K_d$ value that can be accurately determined in a direct binding FP experiment is roughly equal to the concentration of tracer employed. Roehrl, Wang, & Wagner, supra.

Competition fluorescence polarization assays were conducted in black 96-well plates. A solution of 2 nM gp41-5, 1 nM Flu-C38 was prepared in FP assay buffer and arrayed into a 96-well plate (100 µL/well). A second stock plate was prepared containing serial dilutions of peptide inhibitors in DMSO. The peptide stock solutions were transferred to the assay plate (1 µL per well). Each assay plate also included 4 wells each of the following three controls: (1) 100 µL assay buffer+1 µL DMSO; (2) 100 µL of 1 nM Flu-C38+1 µL DMSO as an unbound tracer control; (3) 100 µL of the 2 nM protein/1 nM tracer solution+1 µL DMSO as a bound tracer control. All experimental conditions were carried out in duplicate, and each peptide was assayed in 2-3 independent experiments. Data analysis was carried out in GraphPad Prism. Raw mP data from each experiment were fit to a sigmoidal dose response and normalized to the resulting parameters for the top and bottom of the curve. All experiments included at least one compound showing complete inhibition at the highest concentrations tested. Normalized data from multiple independent runs of the each oligomer were combined and globally fit to an exact analytical expressions for FP competitive binding with $K_i$ as the only floating parameter. The lower bound for $K_i$ measurable in the competition FP experiment was considered to be 0.2 nM, based on the $K_d$ of the tracer. See Roehrl, Wang, & Wagner, supra.

Circular Dichroism Spectroscopy.

Circular dichroism measurements were carried out on an Aviv 202SF Circular Dichroism Spectrophotometer. Samples of each peptide were prepared at 20 µM concentration in PBS. Solutions of 1:1 peptide mixtures were prepared by mixing equal volumes from the same 20 µM stock solutions used for individual peptide measurements. Spectra were recorded in a 1 mm cell with a step size of 1 nm and an averaging time of 5 sec. All spectra are background corrected against buffer measured in the same cell. Thermal melts were carried out in 5-degree increments with an equilibration time of 10 min between each temperature change. Thermal unfolding data were fit to a simple two state folding model Shortle, D.; Meeker, A. K.; Freire, E. *Biochemistry* 1988, 27, 4761-4768) using GraphPad Prism.

Protease Stability.

Stock solutions of the peptides were prepared at a concentration of 25 uM (based on UV absorbance) in TBS. A solution of proteinase K was prepared at a concentration of 50 µg/mL (based on weight to volume) in TBS. For each proteolysis reaction, 40 µL of peptide stock was mixed with 10

µL of proteinase K stock. The reaction was allowed to proceed at room temperature and quenched at the desired time point by addition of 100 µL of 1% TFA in water. 125 µL of the resulting quenched reaction was injected onto an analytical reverse phase HPLC, and the amount of starting peptide present quantified by integration of the peak at 220 nm. Duplicate reactions were run for each time point. Half-lives were determined by fitting time dependent peptide concentration to an exponential decay using GraphPad Prism. Crude samples for some time points were analyzed by MALDI-MS, and the products observed were used to identify amide bonds cleaved in the course of the reaction.

Antiviral Assays.

A cell-to-cell-fusion assay based on the envelope glycoprotein of the HIV-1 clone HXB2 expressed in CHO cells and with U373-MAGI cells as targets was carried out as previously described. (Deng Y Q, Zheng Q, Ketas T J, Moore J P, & Lu M (2007) Protein design of a bacterially expressed HIV-1 gp41 fusion inhibitor. *Biochemistry* 46(14):4360-4369.) All the α/β peptides showed no cytotoxicity at 5 µM, as judged by measuring the basal level of β-galactosidase expression in the U373-MAGI target cells. Inhibition of HIV-1 infectivity was measured on TZM-bl (JC53BL) cells, which express CD4, CXCR4, CCR5 and the luciferase gene under the control of HIV-1 LTR (long terminal repeat). (Wei X P, et al. (2002) Emergence of resistant human immunodeficiency virus type 1 in patients receiving fusion inhibitor (T-20) monotherapy. *Antimicrob Agents Chemother* 46(6): 1896-1905.) Viral stocks produced in PBMC of four HIV-1 strains were used: NL4-3, a clone derived from the X4-tropic T-cell line-adapted isolate IIIB of Clade B; HC4, an X4 primary isolate of Clade B (Trkola A, et al. (1998) Neutralization sensitivity of human immunodeficiency virus type 1 primary isolates to antibodies and CD4-based reagents is independent of coreceptor usage. *J Virol* 72(3):1876-1885); an R5 primary isolate, CC 1/85 (Clade B) (Connor R I, Sheridan K E, Ceradini D, Choe S, & Landau N R (1997) Change in coreceptor use correlates with disease progression in HIV-1-infected individuals. *J Exp Med* 185 (4): 621-628); and another R5 primary isolate, DJ258 (Clade A) (Louwagie J, et al. (1995) Genetic diversity of the envelope glycoprotein from human immunodeficiency virus type-1 isolates of African origin. *J Virol* 69(1):263-271).

Briefly, TZM-bl cells were seeded the day before inoculation at a density of $10^5$ cells/ml, 100 µl/well. Serially diluted peptide in 50 µl (or medium alone as a control) was added to each well. Then the virus, 40 $TCID_{50}$ in 50 µl, or medium only as a background control, was added to each well. On the third day, the wells were inspected by light microscopy. Wells with and without peptide were compared for cell confluency and morphology. No signs of toxicity were discerned at the highest concentrations of peptide used. The infectivity was then quantified in relative light units with the Bright-Glo Luciferase Assay System (Promega Corporation, Madison, Wis., USA), according to the manufacturer's instructions. The experiment was performed three times. The signal of test wells was normalized to that of control wells without inhibitor after background subtraction from both. The % inhibition of infectivity was expressed as a function of the $\log_{10}$ concentration of inhibitor in nM. A four-parameter sigmoid function was fitted to the data in Prism (Graphpad). The $R^2$ values for the fits were 0.95-1.0 for NL4-3; 0.98-1.0 for HC4; 0.95-0.98 for CC 1/85; and 0.92-0.98 for DJ258. Finally, the means±S.E.M. of the $IC_{50}$ values from the individual fits of the three repeat experiments were calculated. The results are depicted graphically in FIGS. 10A (NL4-3), 10B (CC185), 10C (HC4), and 10D (DJ258).

Sequence-Based Design of α/β-Peptides That Mimic BH3 Domains:

As noted above, designing molecules that bind tightly and selectively to a specific site on a protein constitutes a fundamental challenge in molecular recognition. Thus, a systematic approach for identifying suitable molecules would be a distinct advantage. This Example is presented to show that systematic backbone modification throughout a natural protein-binding domain (i.e., sequence-based design) can be used to expeditiously generate α/β-peptide foldamers that bind tightly and selectively to target protein surfaces. In this Example, the sequence-based design approach was used to develop α/β-peptide foldamer ligands for the BH3-recognition cleft of the protein Bcl-$x_L$. Bcl-$x_L$ is a member of the Bcl-2 family, which controls programmed cell death pathways and includes both anti-apoptotic members (e.g., Bcl-2, Bcl-$x_L$, Mcl-1) and pro-apoptotic members (e.g., Bak, Bad, Puma). See Adams & Cory (2007) *Oncogene* 26:1324-1337.

This Example describes a sequence-based design of α/β-peptide ligands for BH3-recognition clefts that differs fundamentally from the structure-based design approaches to foldamer ligands previously pursued by the present inventors and others. The approach involves replacing subsets of regularly spaced α-residues with β-residues bearing the original side chains. Each α to β replacement introduces an extra methylene unit into the backbone. This sequence-based approach does not directly aim to recapitulate the folded structure of an α-peptide prototype, although conformational mimicry is achieved as a byproduct of the replacement strategy employed. As shown in the earlier Example, it has been demonstrated that sequence-based design can be used to generate helix-bundle foldamer quaternary structure from an α-peptide prototype. In this Example, the method is used to mimic the protein-binding behavior of an α-helical BH3 domain. The results demonstrate that sequence-based design is more efficient than structure-based design for generating foldamers that bind tightly to the anti-apoptotic Bcl-2 family proteins, and that sequence-based design can deliver α/β-peptides that display significant resistance to proteolytic degradation.

Puma is a Bcl-2 homolog that binds promiscuously to anti-apoptotic family members. See Chen et al. (2005) *Mol. Cell.* 17:393-403. A 26-residue α-peptide corresponding to the Puma BH3 domain (1') was prepared, along with seven α/β-peptide analogues (2'-8') with the same primary sequence of side chains displayed on different α/β-peptide backbones. See FIG. 7A. Each α/β-peptide contained an ααβααα β backbone repeat which was derived from the heptad pattern common among α-peptide sequences that form α-helices with a well-developed "stripe" of hydrophobic side chains running along one side. See FIG. 7B. Recent crystal structures demonstrate that the ααβααα β backbone allows formation of an α-helix-like conformation. See Horne, Price, Keck, & Gellman (2007) *J. Am. Chem. Soc.* 129:4178-4180. α/β-Peptides 2'-8' represent all possible isomers of the Puma BH3 sequence with the ααβααα β backbone pattern. These oligomers can be viewed as a series of analogs of Puma in which a band of β-residues moves around the helical periphery. See FIG. 7C.

Compounds 1'-8' were tested for their ability to bind to two distinct Bcl-2 family targets, Bcl-xL and Mcl-1. Inhibition constants ($K_i$ for each compound were determined by competition fluorescence polarization (FP) assays (see FIG. 8) with a fluorescently labeled Bak-BH3 peptide as the tracer. The Puma-BH3 peptide (1') showed affinities for Bcl-xL and Mcl-1 that are tighter than can be measured with these FP assays, which is consistent with previous work. $K_i$ values for α/β-peptides 2'-8' vary from less than 1 nM to greater than 100 μM. Variation in the position of β-residue incorporation causes considerable changes in affinity for each protein: greater than 100,000-fold for Bcl-$x_L$ and greater than 700-fold for Mcl-1.

For both protein targets, 4' is the tightest-binding foldamer, with $K_i$<1 nM for Bcl-$x_L$ and $K_i$=150 nM for Mcl-1. It is noteworthy that α/β-peptide 5', which contains β-modifications at critical hydrophobic residues in the Puma BH3 sequence, shows nanomolar affinity for Bcl-$x_L$. These data demonstrate that the location of β-residue incorporation strongly influences Bcl-$x_L$ versus Mcl-1 selectivity among the Puma-derived α/β-peptide isomers, in addition to affinity for these protein targets. For example, 3' shows equal affinity for the two proteins, but 5' displays greater than 4000-fold selectivity for Bcl-$x_L$ over Mcl-1. The validity of the conclusions regarding affinity and selectivity derived from the FP competition assays were tested for α-peptide 1' and α/β-peptides 4' and 5' by performing direct-binding FP measurements with analogs in which the N-terminal acetyl group is replaced with a BODIPY-TMR fluorophore. The $K_d$ values determined by direct binding were consistent with the $K_i$ values obtained from competition data (see Table 5). The differences in absolute values of $K_d$ versus $K_i$ may reflect modest contributions of the appended fluorophore to affinity as measured in the direct binding mode.

TABLE 5

Binding affinity and protease stability data for α-peptide 1' and α/β-peptides 4', 5'.

| | $K_i$[nM][a] | | $K_d$[nM][b] | | $t_{1/2}$[min][c] | |
|---|---|---|---|---|---|---|
| | Bcl-$x_L$ | Mcl-1 | Bcl-$x_L$ | Mcl-1 | Prot. K | Pronase |
| 1' | <1 | <10 | <1 | <2 | 0.7 | 1 |
| 2' | <1 | 150 | 2.2 | 110 | >3000 | 100 |
| 3' | 2.4 | 11000 | 1 | 1100 | 170 | 3.5 |

[a]Inhibition constants determined by competition FP.
[b]Dissociation constants of BODIPY-labeled analogues determined by direct binding FP.
[c]Measured half-life of a 50 μm solution of α-peptide or α/β-peptide in the presence of 10 μg mL$^{-1}$ proteinase K or 5 μg mL$^{-1}$ pronase.

Having established that certain α/β-analogs of the Puma BH3 domain can bind with high affinity to the natural protein partners, an experiment was performed to determine whether the α/β-peptides would be recognized and processed by proteolytic enzymes. α-Peptide 1' and α/β-peptides 4' and 5' were tested for their susceptibility to two proteases with broad substrate profiles: (1) proteinase K, a non-specific serine protease that tends to cleave C-terminal to hydrophobic residues, and (2) "PRONASE"-brand proteinase, a mixture of aggressive endopeptidases and exopeptidases that digests proteins into individual amino acids. ("PRONASE" is a registered trademark of EMD Chemicals, Inc., Gibbstown, N.J.) The results, presented in Table 3, show that the ααβααβ backbone can confer substantial resistance to proteolytic degradation. α/β-Peptide 4', which binds tightly to both Bcl-$x_L$ and Mcl-1, showed a greater than 4000-fold improvement in stability to proteinase K and a 100-fold improvement in stability to "PRONASE"-brand proteinase relative to α-peptide 1'. Analysis of the cleavage products by mass spectrometry indicated that the β-residues tend to protect nearby amide groups from proteolysis, which is consistent with previous reports for isolated α to β$^3$ insertions. α/β-Peptide 5' is more susceptible than is isomer 4' to proteolytic degradation, but 5' nevertheless shows significant improvement relative to α-peptide 1'.

Previous work has suggested that the α-helical propensity of BH3-derived α-peptides may be an important determinant of affinity for anti-apoptotic Bcl-2 family proteins. Circular dichroism (CD) spectroscopy was therefore employed to probe for conformational differences among two of the tight-binding α/β-peptides (4' and 5') and one of the weakest binding analogs (7') described in this Example. Qualitative comparison of CD spectra for 4', 5', and 7' indicates that the large differences in binding affinity among these three isomers cannot be explained by differences in helical propensity. Each of these three α/β-peptides shows a CD minimum at approximately 202 nm with per-residue ellipticity between −13,000 and −15,000 deg cm$^2$ dmol$^{-1}$ in aqueous solution. Helix formation in the ααβααβ backbone is reflected by a strong CD minimum at 206 nm with a maximum magnitude of approximately −40,000 deg cm$^2$ dmol$^{-1}$. Thus, the CD data for 4', 5', and 7' alone in aqueous solution suggest relatively low population of the helical state. Similarly, the CD signature for Puma α-peptide 1 in aqueous solution ($[\theta]_{222}$=−10,000 deg cm$^2$ dmol$^{-1}$ res$^{-1}$) suggests little α-helical content. Without being limited to any specific mechanism, on the basis of the established precedent for induction of α-helix formation upon binding of BH3 domain α-peptides to Bcl-$x_L$ and Mcl-1, the co-inventors hypothesize that α/βpeptides such as 4' and 5' are induced to adopt helical conformations upon binding to protein partners.

The work reported herein demonstrates that a straightforward principle of sequence-based design can be used to convert a helical α-peptide ligand into an α/β-peptide with comparable binding affinity for protein targets and substantially improved proteolytic stability. The strategy disclosed and claimed herein is a fundamental departure from previous work on the development of foldamer-based inhibitors of protein-protein interactions. The sequence-based approach disclosed herein has been shown by these Examples to be more efficient than the structure-based approach for generating foldamer mimics of α-helices.

In short, evaluating a series of just seven α/β-peptides designed purely on the basis of primary sequence information led to a compound that rivals the best of the previously described chimeric α/β+α ligands in binding affinity for Bcl-$x_L$. See Sadowsky, Schmitt, Lee, Umezawa, Wang, Tomita, and Gellman (2005) J. Am. Chem. Soc 127:11966-11968; Sadowsky, Fairlie, Hadley, Lee, Umezawa, Nikolovska-Coleska, Wang, Huang, Tomita, and Gellman (2007) J. Am. Chem. Soc. 129:139-154; and Sadowsky, Murray, Tomita, and Gellman (2007) ChemBioChem 8:903-916. Moreover, the best α/β-peptide binds moderately well to Mcl-1, a biomedically important Bcl-2 family protein that is not targeted by oligomers identified through structure-based design. The implementation of multiple and systematic α-residue to β-residue replacements throughout a peptide sequence (7 of 26 positions substituted in the Puma BH3 domain) constitutes a significant advance beyond earlier precedents in the design of bioactive, proteolytically stable oligomers. The finding that one version of this substitution pattern is well-tolerated in terms of binding to anti-apoptotic proteins is surprising and noteworthy.

The sequence-based design illustrated herein can be implemented with commercially available α- and β-amino acid monomers and standard automated peptide synthesis methods. Thus, it is straightforward for others to undertake analogous efforts.

Comparisons of Chimeric α-α/β Foldamers:

Peptides 12, 13, and 8, below are chimeric α+α/β foldamers of a lead α/β foldamer 10. These peptides were created to determine the effect of beta substitution in the region near the N terminus. The beta residues were sequentially subtracted in the "f" and "c" positions along the heptad. The effect of α to β substitutions was monitored with a previously reported Fluorescence Polarization (FP) competition assay. (Frey, G.; Rits-Volloch, S.; Zhang, X. Q.; Schooley, R. T.; Chen, B.; Harrison, S. C. Small molecules that bind the inner core of gp41 and inhibit HIV envelope-mediated fusion. *Proc. Natl. Acad. Sci.,* 2006, 103, 13938-43.) The results suggest that β substitution has a slow, cumulative effect of decreasing the binding. Chimeric α+α/β Foldamers, Subtracting β Residues from the "f" and "c" Positions Near the N-Terminus:

```
        fgabcdefgabcdefg . . .
                                        (SEQ. ID. NO: 10)
10:   Ac-TTWEXWDZAIAEYAXRIEXLIZAAQEQQEKNEXALZEL-NH₂

(SEQ. ID. NO: 25)
12:   Ac-TTWEAWDZAIAEYAXRIEXLIZAAQEQQEKNEXALZEL-NH₂

(SEQ. ID. NO: 26)
13:   Ac-TTWEAWDRAIAEYAXRIEXLIZAAQEQQEKNEXALZEL-NH₂

(SEQ. ID. NO: 8)
8:    Ac-TTWEAWDRAIAEYAXRIEXLIZAAQEQQEKNEXALZEL-NH₂
```

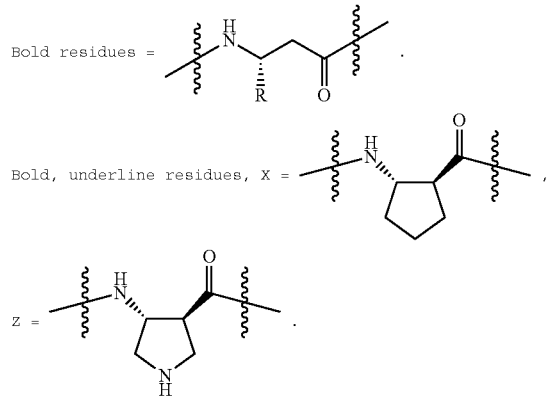

$K_i$ (nM):
compound 10 = 9
compound 12 = 8
compound 13 = 0.8
compound 8 = 0.3

To determine if β substitution disrupted binding in one region of the peptide, α+α/β chimeric peptides were synthesized with different alpha segments substituted in the beta stripe. The regions of focus were near the N terminus 8, middle 14, and C terminus of the peptide 15. The FP data showed that introducing an alpha segment did increase binding of the foldamer; however, the $K_i$'s were all very similar, which suggested that β substitution slowly disrupted the binding across the entire length of the helix and not in a particular region.

Chimeric α+α/β Foldamers, Substitution of α Segments in the N-Terminal, Middle, and C-Terminal Regions:

```
                                        (SEQ. ID. NO: 8)
8:    Ac-TTWEAWDRAIAEYAXRIEXLIZAAQEQQEKNEXALZEL-NH₂

(SEQ. ID. NO: 27)
14:   Ac-TTWEXWDZAIAEYAARIEALIRAAQEQQEKNEXALZEL-NH₂

(SEQ. ID. NO: 28)
15:   Ac-TTWEXWDZAIAEYAXRIEXLIZAAQEQQEKNEAALREL-NH₂
```

$K_i$ (nM):
compound 8 = 0.3
compound 14 = 1.4
compound 15 = 0.2

Foldamer 10 showed that cyclic residues effectively constrained the Cα-Cβ torsional angles to aid in folding, but other tactics could be used to constrain a helix. Salt bridges of α residues were effective at pre-forming a helices. See Nishikawa, H.; Nakamura, S.; Kodama, E.; Ito, S.; Kajiwara, K.; Izumi, K.; Sakagami, Y.; Oishi, S.; Ohkubo, T.; Kobayashi, Y.; Otaka, A.; Fujii, N.; Matsuoka, M. Electrostatically constrained alpha-helical peptide inhibits replication of HIV-1 resistant to enfuvirtide. *Int. J. Biochem. Cell Biol.* 2009, 41, 891-9. Another design strategy positioned a stripe of arginines in the i position which interacted with a stripe of glutamates in the i+4 position, favoring an α helical structure. See Burkhard, P.; Meier, M.; Lustig, A. Design of a minimal protein oligomerization domain by a structural approach. *Prot. Sci.,* 2000, 9, 2294-2301.

The following peptide 17 examined the ability of beta residues to form salt bridges that pre-organize a helix. Because it was previously found that the "f" and "c" positions were the most compliant with beta substitution, β-hArg was placed in the "f" position and β-hGlu was placed in the "c" position to maximize i and i+4 interactions. Peptide 16 was created to test if both cyclic beta residues and salt bridging beta residues worked synergistically in the beta stripe. The FP data suggested that α/β foldamers 16 and 17 were approximately equal inhibitors to foldamer 10.

```
                                        (SEQ. ID. NO: 10)
        fgabcdefgabcdefg . . .
10:   Ac-TTWEXWDZAIAEYAXRIEXLIZAAQEQQEKNEXALZEL-NH₂

(SEQ. ID. NO: 29)
16:   Ac-RTWEEWDRAIAEYAXRIEXLIZAAQXQQZKNEXALZEL-NH₂

(SEQ. ID. NO: 30)
17:   Ac-RTWEEWDRAIAEYARRIEELIRAAQEQQRKNEEALREL-NH₂
```

$K_i$ (nM):
compound 10 = 9
compound 16 = 3
compound 17 = 11

These results are significant in that compound 17 does not contain any cyclically constrained residues. While not being limited to any underlying mechanism or phenomenon, it appears that conformational stability is achieved by incorporating ion pairs along one side of the helical conformation.

What is claimed is:

1. A method of fabricating a biologically active, proteoloytic-resistant, unnatural polypeptide, the method comprising: fabricating a synthetic polypeptide that has an amino acid sequence that corresponds to a sequence of a biologically active polypeptide or fragment thereof, wherein
   (i) in the synthetic polypeptide from about 14% to about 50% of the α-amino acid residues found in the biologically active polypeptide or fragment are replaced with analogous β-amino acid residues, wherein at least one of the β-amino acid residues is cyclically constrained via a ring encompassing its $\beta^2$ and $\beta^3$ carbon atoms;
   (ii) in the synthetic polypeptide the β-amino acid residues and the α-amino acid residues are distributed in a pattern that repeats at least once, wherein the pattern of β-amino acid residues and α-amino acid residues is selected from the group consisting of (ααααααβ), (αααααβ), (ααααβ), (αααβ), and (ααβαβαβ).

2. The method of fabricating biologically active, unnatural polypeptides according to claim 1, wherein in a folded structure adopted by the polypeptides, the repeating pattern disposes the β-amino acid residues in alignment along one side of the folded molecular structure when the unnatural polypeptides adopt a helical conformation.

3. The method of fabricating biologically active, unnatural polypeptides according to claim 1, wherein the method comprises fabricating a synthetic polypeptide having from about 20 residues to about 50 residues.

4. The method of fabricating biologically active, unnatural polypeptides according to claim 1, wherein the biologically active polypeptide or pharmaceutical salt thereof comprises between about 10 residues to about 100 residues and comprises at least two β-amino acid residues.

5. The method of fabricating biologically active, unnatural polypeptides according to claim 1, wherein at least one of the β-amino acid residues is unsubstituted at its $\beta^2$ or $\beta^3$ carbon atoms.

6. A method of fabricating biologically active, unnatural polypeptides, the method comprising:
   (a) selecting a biologically active polypeptide or biologically active fragment thereof having an amino acid sequence comprising α-amino acid residues; and
   (b) fabricating a synthetic polypeptide that has an amino acid sequence that corresponds to the sequence of the biologically active polypeptide or fragment of step (a), wherein
       (i) in the synthetic polypeptide between about 14% and about 50% of the α-amino acid residues found in the biologically active polypeptide or fragment of step (a) are replaced with β-amino acid residues, wherein at least one of the α-amino acid residues is replaced with at least one β-amino acid residue that is cyclically constrained via a ring encompassing its $\beta^2$ and $\beta^3$ carbon atoms;
       (ii) in the synthetic polypeptide the β-amino acid residues and the α-amino acid residues are distributed in a repeating pattern; and
       (iii) the synthetic polypeptide has a length of from about 10 residues to about 100 residues and comprises at least two β-amino acid residues;
   wherein the synthetic polypeptide that is fabricated has a repeating pattern of α-amino acid residues and β-amino acid residues selected from the group consisting of (ααααααβ), (αααααβ), (ααααβ), (αααβ), and (ααβαβαβ).

* * * * *

SEQUENCE LISTING

<160> NUMBER OF SEQ ID NOS: 30

<210> SEQ ID NO 1
<211> LENGTH: 36
<212> TYPE: PRT

-continued

```
<213> ORGANISM: Artificial
<220> FEATURE:
<223> OTHER INFORMATION: Synthetic polypeptide

<400> SEQUENCE: 1

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 2
<211> LENGTH: 34
<212> TYPE: PRT
<213> ORGANISM: Artificial
<220> FEATURE:
<223> OTHER INFORMATION: Synthetic polypeptide

<400> SEQUENCE: 2

Trp Met Glu Trp Asp Arg Glu Ile Asn Asn Tyr Thr Ser Leu Ile His
1               5                   10                  15

Ser Leu Ile Glu Glu Ser Gln Asn Gln Gln Lys Asn Glu Gln Glu
            20                  25                  30

Leu Leu

<210> SEQ ID NO 3
<211> LENGTH: 38
<212> TYPE: PRT
<213> ORGANISM: Artificial
<220> FEATURE:
<223> OTHER INFORMATION: Synthetic polypeptide

<400> SEQUENCE: 3

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Asn Glu
            20                  25                  30

Ala Ala Leu Arg Glu Leu
        35

<210> SEQ ID NO 4
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-T
<220> FEATURE:
<221> NAME/KEY: MISC_FEATURE
<222> LOCATION: (5)..(5)
<223> OTHER INFORMATION: Beta3-A
<220> FEATURE:
<221> NAME/KEY: MISC_FEATURE
<222> LOCATION: (8)..(8)
<223> OTHER INFORMATION: Beta3-R
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: Beta3-A
```

```
<220> FEATURE:
<221> NAME/KEY: MISC_FEATURE
<222> LOCATION: (19)..(19)
<223> OTHER INFORMATION: Beta3-A
<220> FEATURE:
<221> NAME/KEY: MISC_FEATURE
<222> LOCATION: (22)..(22)
<223> OTHER INFORMATION: Beta3-R
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: Beta3-A
<220> FEATURE:
<221> NAME/KEY: MISC_FEATURE
<222> LOCATION: (36)..(36)
<223> OTHER INFORMATION: Beta3-R

<400> SEQUENCE: 4

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Asn Glu
            20                  25                  30

Ala Ala Leu Arg Glu Leu
        35

<210> SEQ ID NO 5
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (22)..(22)
<223> OTHER INFORMATION: Beta3-R
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: Beta3-A
<220> FEATURE:
<221> NAME/KEY: MISC_FEATURE
<222> LOCATION: (36)..(36)
<223> OTHER INFORMATION: Beta3-R

<400> SEQUENCE: 5

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Asn Glu
            20                  25                  30

Ala Ala Leu Arg Glu Leu
        35

<210> SEQ ID NO 6
<211> LENGTH: 38
<212> TYPE: PRT
```

<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (15)..(15)
<223> OTHER INFORMATION: Beta3-A
<220> FEATURE:
<221> NAME/KEY: MISC_FEATURE
<222> LOCATION: (19)..(19)
<223> OTHER INFORMATION: Beta3-A
<220> FEATURE:
<221> NAME/KEY: MISC_FEATURE
<222> LOCATION: (22)..(22)
<223> OTHER INFORMATION: Beta3-R
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: Beta3-A
<220> FEATURE:
<221> NAME/KEY: MISC_FEATURE
<222> LOCATION: (36)..(36)
<223> OTHER INFORMATION: Beta3-R

<400> SEQUENCE: 6

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Asn Glu
            20                  25                  30

Ala Ala Leu Arg Glu Leu
        35

<210> SEQ ID NO 7
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: Beta3-R
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: Beta3-R -continued

```
<400> SEQUENCE: 7

Thr Thr Trp Glu Ala Trp Asp Arg Ala Ile Ala Glu Tyr Ala Xaa Arg
1               5                   10                  15

Ile Glu Xaa Leu Ile Arg Ala Ala Gln Glu Gln Gln Glu Lys Asn Glu
            20                  25                  30

Xaa Ala Leu Arg Glu Leu
        35

<210> SEQ ID NO 8
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: trans-3-aminopyrrolidine-4-carboxylic acid
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: trans-3-aminopyrrolidine-4-carboxylic acid

<400> SEQUENCE: 8

Thr Thr Trp Glu Ala Trp Asp Arg Ala Ile Ala Glu Tyr Ala Xaa Arg
1               5                   10                  15

Ile Glu Xaa Leu Ile Glx Ala Ala Gln Glu Gln Gln Glu Lys Asn Glu
            20                  25                  30

Xaa Ala Leu Glx Glu Leu
        35

<210> SEQ ID NO 9
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-T
<220> FEATURE:
<221> NAME/KEY: MISC_FEATURE
<222> LOCATION: (5)..(5)
<223> OTHER INFORMATION: trans-2-aminocyclopentanecarboxylic acid
<220> FEATURE:
<221> NAME/KEY: MISC_FEATURE
<222> LOCATION: (8)..(8)
<223> OTHER INFORMATION: Beta3-R
<220> FEATURE:
<221> NAME/KEY: MISC_FEATURE
```

-continued

```
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: Beta3-R
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: Beta3-R

<400> SEQUENCE: 9

Thr Thr Trp Glu Xaa Trp Asp Arg Ala Ile Ala Glu Tyr Ala Xaa Arg
1               5                   10                  15

Ile Glu Xaa Leu Ile Arg Ala Ala Gln Glu Gln Gln Glu Lys Asn Glu
            20                  25                  30

Xaa Ala Leu Arg Glu Leu
        35

<210> SEQ ID NO 10
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-T
<220> FEATURE:
<221> NAME/KEY: MISC_FEATURE
<222> LOCATION: (5)..(5)
<223> OTHER INFORMATION: trans-2-aminocyclopentanecarboxylic acid
<220> FEATURE:
<221> NAME/KEY: MISC_FEATURE
<222> LOCATION: (8)..(8)
<223> OTHER INFORMATION: trans-3-aminopyrrolidine-4-carboxylic acid
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: trans-3-aminopyrrolidine-4-carboxylic acid
<220> FEATURE:
<221> NAME/KEY: MISC_FEATURE
```

```
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: trans-3-aminopyrrolidine-4-carboxylic acid

<400> SEQUENCE: 10

Thr Thr Trp Glu Xaa Trp Asp Glx Ala Ile Ala Glu Tyr Ala Xaa Arg
1               5                   10                  15

Ile Glu Xaa Leu Ile Glx Ala Ala Gln Glu Gln Gln Glu Lys Asn Glu
            20                  25                  30

Xaa Ala Leu Glx Glu Leu
        35

<210> SEQ ID NO 11
<211> LENGTH: 28
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Beta3-E
<220> FEATURE:
<221> NAME/KEY: MISC_FEATURE
<222> LOCATION: (5)..(5)
<223> OTHER INFORMATION: trans-2-aminocyclopentanecarboxylic acid
<220> FEATURE:
<221> NAME/KEY: MISC_FEATURE
<222> LOCATION: (9)..(9)
<223> OTHER INFORMATION: trans-2-aminocyclopentanecarboxylic acid
<220> FEATURE:
<221> NAME/KEY: MISC_FEATURE
<222> LOCATION: (12)..(12)
<223> OTHER INFORMATION: trans-3-aminopyrrolidine-4-carboxylic acid
<220> FEATURE:
<221> NAME/KEY: MISC_FEATURE
<222> LOCATION: (16)..(16)
<223> OTHER INFORMATION: Beta3-E
<220> FEATURE:
<221> NAME/KEY: MISC_FEATURE
<222> LOCATION: (19)..(19)
<223> OTHER INFORMATION: Beta3-E
<220> FEATURE:
<221> NAME/KEY: MISC_FEATURE
<222> LOCATION: (23)..(23)
<223> OTHER INFORMATION: trans-2-aminocyclopentanecarboxylic acid
<220> FEATURE:
<221> NAME/KEY: MISC_FEATURE
<222> LOCATION: (26)..(26)
<223> OTHER INFORMATION: trans-3-aminopyrrolidine-4-carboxylic acid

<400> SEQUENCE: 11

Ala Glu Tyr Ala Xaa Arg Ile Glu Xaa Leu Ile Glx Ala Ala Gln Glu
1               5                   10                  15

Gln Gln Glu Lys Asn Glu Xaa Ala Leu Glx Glu Leu
            20                  25

<210> SEQ ID NO 12
<211> LENGTH: 36
<212> TYPE: PRT
<213> ORGANISM: Artificial
```

```
<220> FEATURE:
<223> OTHER INFORMATION: Synthetic polypeptide

<400> SEQUENCE: 12

Ser Gly Ile Val Gln Gln Gln Asn Asn Leu Leu Arg Ala Ile Glu Ala
1               5                   10                  15
Gln Gln His Leu Leu Gln Leu Thr Val Trp Gly Ile Lys Gln Leu Gln
            20                  25                  30
Ala Arg Ile Leu
        35

<210> SEQ ID NO 13
<211> LENGTH: 34
<212> TYPE: PRT
<213> ORGANISM: Artificial
<220> FEATURE:
<223> OTHER INFORMATION: Synthetic polypeptide

<400> SEQUENCE: 13

Trp Met Glu Trp Asp Arg Glu Ile Asn Asn Tyr Thr Ser Leu Ile His
1               5                   10                  15
Ser Leu Ile Glu Glu Ser Gln Asn Gln Gln Glu Lys Asn Glu Gln Glu
            20                  25                  30
Leu Leu

<210> SEQ ID NO 14
<211> LENGTH: 38
<212> TYPE: PRT
<213> ORGANISM: Artificial
<220> FEATURE:
<223> OTHER INFORMATION: Synthetic polypeptide

<400> SEQUENCE: 14

Trp Met Glu Trp Asp Arg Glu Ile Asn Asn Tyr Thr Ser Leu Ile His
1               5                   10                  15
Ser Leu Ile Glu Glu Ser Gln Asn Gln Gln Glu Lys Asn Glu Gln Glu
            20                  25                  30
Leu Leu Glu Leu Asp Lys
        35

<210> SEQ ID NO 15
<211> LENGTH: 26
<212> TYPE: PRT
<213> ORGANISM: Artificial
<220> FEATURE:
<223> OTHER INFORMATION: Synthetic polypeptide

<400> SEQUENCE: 15

Glu Glu Gln Trp Ala Arg Glu Ile Gly Ala Gln Leu Arg Arg Met Ala
1               5                   10                  15
Asp Asp Leu Asn Ala Gln Tyr Glu Arg Arg
            20                  25

<210> SEQ ID NO 16
<211> LENGTH: 26
<212> TYPE: PRT
<213> ORGANISM: Artificial
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Beta3-Q
<220> FEATURE:
```

-continued

```
<221> NAME/KEY: misc_feature
<222> LOCATION: (6)..(6)
<223> OTHER INFORMATION: Beta3-R
<220> FEATURE:
<221> NAME/KEY: MISC_FEATURE
<222> LOCATION: (6)..(6)
<220> FEATURE:
<221> NAME/KEY: misc_feature
<222> LOCATION: (10)..(10)
<223> OTHER INFORMATION: Beta3-A
<220> FEATURE:
<221> NAME/KEY: misc_feature
<222> LOCATION: (13)..(13)
<223> OTHER INFORMATION: Beta3-R
<220> FEATURE:
<221> NAME/KEY: misc_feature
<222> LOCATION: (17)..(17)
<223> OTHER INFORMATION: Beta3-D
<220> FEATURE:
<221> NAME/KEY: misc_feature
<222> LOCATION: (20)..(20)
<223> OTHER INFORMATION: Beta3-N
<220> FEATURE:
<221> NAME/KEY: misc_feature
<222> LOCATION: (24)..(24)
<223> OTHER INFORMATION: Beta3-E

<400> SEQUENCE: 16

Glu Glu Gln Trp Ala Arg Glu Ile Gly Ala Gln Leu Arg Arg Met Ala
1               5                   10                  15

Asp Asp Leu Asn Ala Gln Tyr Glu Arg Arg
            20                  25

<210> SEQ ID NO 17
<211> LENGTH: 26
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Beta3-Q
<220> FEATURE:
<221> NAME/KEY: MISC_FEATURE
<222> LOCATION: (7)..(7)
<223> OTHER INFORMATION: Beta3-E
<220> FEATURE:
<221> NAME/KEY: MISC_FEATURE
<222> LOCATION: (10)..(10)
<223> OTHER INFORMATION: Beta3-A
<220> FEATURE:
<221> NAME/KEY: MISC_FEATURE
<222> LOCATION: (14)..(14)
<223> OTHER INFORMATION: Beta3-R
<220> FEATURE:
<221> NAME/KEY: MISC_FEATURE
<222> LOCATION: (17)..(17)
<223> OTHER INFORMATION: Beta3-D
<220> FEATURE:
<221> NAME/KEY: MISC_FEATURE
<222> LOCATION: (21)..(21)
<223> OTHER INFORMATION: Beta3-A
<220> FEATURE:
<221> NAME/KEY: MISC_FEATURE
<222> LOCATION: (24)..(24)
<223> OTHER INFORMATION: Beta3-E

<400> SEQUENCE: 17

Glu Glu Gln Trp Ala Arg Glu Ile Gly Ala Gln Leu Arg Arg Met Ala
1               5                   10                  15

Asp Asp Leu Asn Ala Gln Tyr Glu Arg Arg
            20                  25
```

<210> SEQ ID NO 18
<211> LENGTH: 26
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Beta3-W
<220> FEATURE:
<221> NAME/KEY: MISC_FEATURE
<222> LOCATION: (7)..(7)
<223> OTHER INFORMATION: Beta3-E
<220> FEATURE:
<221> NAME/KEY: MISC_FEATURE
<222> LOCATION: (11)..(11)
<223> OTHER INFORMATION: Beta3-Q
<220> FEATURE:
<221> NAME/KEY: MISC_FEATURE
<222> LOCATION: (14)..(14)
<223> OTHER INFORMATION: Beta3-R
<220> FEATURE:
<221> NAME/KEY: MISC_FEATURE
<222> LOCATION: (18)..(18)
<223> OTHER INFORMATION: Beta3-D
<220> FEATURE:
<221> NAME/KEY: MISC_FEATURE
<222> LOCATION: (21)..(21)
<223> OTHER INFORMATION: Beta3-A
<220> FEATURE:
<221> NAME/KEY: MISC_FEATURE
<222> LOCATION: (25)..(25)
<223> OTHER INFORMATION: Beta3-R

<400> SEQUENCE: 18

Glu Glu Gln Trp Ala Arg Glu Ile Gly Ala Gln Leu Arg Arg Met Ala
1               5                   10                  15

Asp Asp Leu Asn Ala Gln Tyr Glu Arg Arg
            20                  25

<210> SEQ ID NO 19
<211> LENGTH: 26
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-E
<220> FEATURE:
<221> NAME/KEY: MISC_FEATURE
<222> LOCATION: (4)..(4)
<223> OTHER INFORMATION: Beta3-W
<220> FEATURE:
<221> NAME/KEY: MISC_FEATURE
<222> LOCATION: (8)..(8)
<223> OTHER INFORMATION: Beta3-I
<220> FEATURE:
<221> NAME/KEY: MISC_FEATURE
<222> LOCATION: (11)..(11)
<223> OTHER INFORMATION: Beta3-Q
<220> FEATURE:
<221> NAME/KEY: MISC_FEATURE
<222> LOCATION: (15)..(15)
<223> OTHER INFORMATION: Beta3-M
<220> FEATURE:
<221> NAME/KEY: MISC_FEATURE
<222> LOCATION: (18)..(18)
<223> OTHER INFORMATION: Beta3-D
<220> FEATURE:
<221> NAME/KEY: MISC_FEATURE
<222> LOCATION: (22)..(22)
<223> OTHER INFORMATION: Beta3-Q

```
<220> FEATURE:
<221> NAME/KEY: MISC_FEATURE
<222> LOCATION: (25)..(25)
<223> OTHER INFORMATION: Beta3-R

<400> SEQUENCE: 19

Glu Glu Gln Trp Ala Arg Glu Ile Gly Ala Gln Leu Arg Arg Met Ala
1               5                   10                  15

Asp Asp Leu Asn Ala Gln Tyr Glu Arg Arg
            20                  25

<210> SEQ ID NO 20
<211> LENGTH: 26
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-E
<220> FEATURE:
<221> NAME/KEY: MISC_FEATURE
<222> LOCATION: (5)..(5)
<223> OTHER INFORMATION: Beta3-A
<220> FEATURE:
<221> NAME/KEY: MISC_FEATURE
<222> LOCATION: (8)..(8)
<223> OTHER INFORMATION: Beta3-I
<220> FEATURE:
<221> NAME/KEY: MISC_FEATURE
<222> LOCATION: (12)..(12)
<223> OTHER INFORMATION: Beta3-L
<220> FEATURE:
<221> NAME/KEY: MISC_FEATURE
<222> LOCATION: (15)..(15)
<223> OTHER INFORMATION: Beta3-M
<220> FEATURE:
<221> NAME/KEY: MISC_FEATURE
<222> LOCATION: (19)..(19)
<223> OTHER INFORMATION: Beta3-L
<220> FEATURE:
<221> NAME/KEY: MISC_FEATURE
<222> LOCATION: (22)..(22)
<223> OTHER INFORMATION: Beta3-Q
<220> FEATURE:
<221> NAME/KEY: MISC_FEATURE
<222> LOCATION: (26)..(26)
<223> OTHER INFORMATION: Beta3-R

<400> SEQUENCE: 20

Glu Glu Gln Trp Ala Arg Glu Ile Gly Ala Gln Leu Arg Arg Met Ala
1               5                   10                  15

Asp Asp Leu Asn Ala Gln Tyr Glu Arg Arg
            20                  25

<210> SEQ ID NO 21
<211> LENGTH: 26
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Beta3-E
<220> FEATURE:
<221> NAME/KEY: MISC_FEATURE
<222> LOCATION: (5)..(5)
<223> OTHER INFORMATION: Beta3-A
<220> FEATURE:
<221> NAME/KEY: MISC_FEATURE
<222> LOCATION: (9)..(9)
```

<223> OTHER INFORMATION: Beta3-G
<220> FEATURE:
<221> NAME/KEY: MISC_FEATURE
<222> LOCATION: (12)..(12)
<223> OTHER INFORMATION: Beta3-L
<220> FEATURE:
<221> NAME/KEY: MISC_FEATURE
<222> LOCATION: (16)..(16)
<223> OTHER INFORMATION: Beta3-A
<220> FEATURE:
<221> NAME/KEY: MISC_FEATURE
<222> LOCATION: (19)..(19)
<223> OTHER INFORMATION: Beta3-L
<220> FEATURE:
<221> NAME/KEY: MISC_FEATURE
<222> LOCATION: (23)..(23)
<223> OTHER INFORMATION: Beta3-Y
<220> FEATURE:
<221> NAME/KEY: MISC_FEATURE
<222> LOCATION: (26)..(26)
<223> OTHER INFORMATION: Beta3-R

<400> SEQUENCE: 21

Glu Glu Gln Trp Ala Arg Glu Ile Gly Ala Gln Leu Arg Arg Met Ala
1               5                   10                  15
Asp Asp Leu Asn Ala Gln Tyr Glu Arg Arg
            20                  25

<210> SEQ ID NO 22
<211> LENGTH: 26
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Beta3-E
<220> FEATURE:
<221> NAME/KEY: MISC_FEATURE
<222> LOCATION: (6)..(6)
<223> OTHER INFORMATION: Beta3-R
<220> FEATURE:
<221> NAME/KEY: MISC_FEATURE
<222> LOCATION: (9)..(9)
<223> OTHER INFORMATION: Beta3-G
<220> FEATURE:
<221> NAME/KEY: MISC_FEATURE
<222> LOCATION: (13)..(13)
<223> OTHER INFORMATION: Beta3-R
<220> FEATURE:
<221> NAME/KEY: MISC_FEATURE
<222> LOCATION: (16)..(16)
<223> OTHER INFORMATION: Beta3-A
<220> FEATURE:
<221> NAME/KEY: MISC_FEATURE
<222> LOCATION: (20)..(20)
<223> OTHER INFORMATION: Beta3-N
<220> FEATURE:
<221> NAME/KEY: MISC_FEATURE
<222> LOCATION: (23)..(23)
<223> OTHER INFORMATION: Beta3-Y

<400> SEQUENCE: 22

Glu Glu Gln Trp Ala Arg Glu Ile Gly Ala Gln Leu Arg Arg Met Ala
1               5                   10                  15
Asp Asp Leu Asn Ala Gln Tyr Glu Arg Arg
            20                  25

<210> SEQ ID NO 23
<211> LENGTH: 38
<212> TYPE: PRT
<213> ORGANISM: Artificial

```
<220> FEATURE:
<223> OTHER INFORMATION: Synthetic polypeptide

<400> SEQUENCE: 23

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys
        35

<210> SEQ ID NO 24
<211> LENGTH: 199
<212> TYPE: PRT
<213> ORGANISM: Human immunodeficiency virus
<300> PUBLICATION INFORMATION:
<301> AUTHORS: Frey, Rits-Vollovh, Zhang, Schooley, Chen, Harrison
<302> TITLE: Small molecules that bind the inner core of gp41 and
       inhibit HIV envelope-mediated fusion
<303> JOURNAL: Proc. Natl. Acad. Sci. USA
<304> VOLUME: 103
<305> ISSUE: 38
<306> PAGES: 13938-13943
<307> DATE: 2006-09-19
<313> RELEVANT RESIDUES IN SEQ ID NO: (1)..(199)

<400> SEQUENCE: 24

Met Ser Gly Ile Val Gln Gln Gln Asn Asn Leu Leu Arg Ala Ile Glu
1               5                   10                  15

Ala Gln Gln His Leu Leu Gln Leu Thr Val Trp Gly Ile Lys Gln Leu
            20                  25                  30

Gln Ala Arg Ile Leu Ser Gly Gly Ser Gly Gly Trp Met Glu Trp Asp
        35                  40                  45

Arg Glu Ile Asn Asn Tyr Thr Ser Leu Ile His Ser Leu Ile Glu Glu
    50                  55                  60

Ser Gln Asn Gln Gln Glu Lys Asn Glu Gln Glu Leu Leu Gly Gly Ser
65                  70                  75                  80

Gly Gly Ser Gly Ile Val Gln Gln Gln Asn Asn Leu Leu Arg Ala Ile
                85                  90                  95

Glu Ala Gln Gln His Leu Leu Gln Leu Thr Val Trp Gly Ile Lys Gln
            100                 105                 110

Leu Gln Ala Arg Ile Leu Ser Gly Gly Ser Gly Gly Trp Met Glu Trp
        115                 120                 125

Asp Arg Glu Ile Asn Asn Tyr Thr Ser Leu Ile His Ser Leu Ile Glu
    130                 135                 140

Glu Ser Gln Asn Gln Gln Glu Lys Asn Glu Gln Glu Leu Leu Gly Gly
145                 150                 155                 160

Ser Gly Gly Ser Gly Ile Val Gln Gln Gln Asn Asn Leu Leu Arg Ala
                165                 170                 175

Ile Glu Ala Gln Gln His Leu Leu Gln Leu Thr Val Trp Gly Ile Lys
            180                 185                 190

Gln Leu Gln Ala Arg Ile Leu
        195

<210> SEQ ID NO 25
<211> LENGTH: 38
<212> TYPE: PRT
<213> ORGANISM: Artificial
<220> FEATURE:
<223> OTHER INFORMATION: Synthetic polypeptide
<220> FEATURE:
```

```
<221> NAME/KEY: MISC_FEATURE
<222> LOCATION: (8)..(8)
<223> OTHER INFORMATION: trans-3-aminopyrrolidine-4-carboxylic acid
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: trans-3-aminopyrrolidine-4-carboxylic acid
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: trans-3-aminopyrrolidine-4-carboxylic acid

<400> SEQUENCE: 25

Thr Thr Trp Glu Ala Trp Asp Glx Ala Ile Ala Glu Tyr Ala Xaa Arg
1               5                   10                  15

Ile Glu Xaa Leu Ile Glx Ala Ala Gln Glu Gln Gln Glu Lys Asn Glu
            20                  25                  30

Xaa Ala Leu Glx Glu Leu
        35

<210> SEQ ID NO 26
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: trans-3-aminopyrrolidine-4-carboxylic acid
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
```

<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: trans-3-aminopyrrolidine-4-carboxylic acid

<400> SEQUENCE: 26

Thr Thr Trp Glu Ala Trp Asp Arg Ala Ile Ala Glu Tyr Ala Xaa Arg
1               5                   10                  15

Ile Glu Xaa Leu Ile Glx Ala Ala Gln Glu Gln Gln Glu Lys Asn Glu
            20                  25                  30

Xaa Ala Leu Glx Glu Leu
        35

<210> SEQ ID NO 27
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-T
<220> FEATURE:
<221> NAME/KEY: MISC_FEATURE
<222> LOCATION: (5)..(5)
<223> OTHER INFORMATION: trans-2-aminocyclopentanecarboxylic acid
<220> FEATURE:
<221> NAME/KEY: MISC_FEATURE
<222> LOCATION: (8)..(8)
<223> OTHER INFORMATION: trans-3-aminopyrrolidine-4-carboxylic acid
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-E
<220> FEATURE:
<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: trans-3-aminopyrrolidine-4-carboxylic acid

<400> SEQUENCE: 27

Thr Thr Trp Glu Xaa Trp Asp Glx Ala Ile Ala Glu Tyr Ala Ala Arg
1               5                   10                  15

Ile Glu Ala Leu Ile Arg Ala Ala Gln Glu Gln Gln Glu Lys Asn Glu
            20                  25                  30

Xaa Ala Leu Glx Glu Leu
        35

<210> SEQ ID NO 28
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE -continued

```
<222> LOCATION: (1)..(1)
<223> OTHER INFORMATION: Beta3-T
<220> FEATURE:
<221> NAME/KEY: MISC_FEATURE
<222> LOCATION: (5)..(5)
<223> OTHER INFORMATION: trans-2-aminocyclopentanecarboxylic acid
<220> FEATURE:
<221> NAME/KEY: MISC_FEATURE
<222> LOCATION: (8)..(8)
<223> OTHER INFORMATION: trans-3-aminopyrrolidine-4-carboxylic acid
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: trans-3-aminopyrrolidine-4-carboxylic acid

<400> SEQUENCE: 28

Thr Thr Trp Glu Xaa Trp Asp Glx Ala Ile Ala Glu Tyr Ala Xaa Arg
1               5                   10                  15

Ile Glu Xaa Leu Ile Glx Ala Ala Gln Glu Gln Gln Glu Lys Asn Glu
            20                  25                  30

Ala Ala Leu Arg Glu Leu
        35

<210> SEQ ID NO 29
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-R
<220> FEATURE:
<221> NAME/KEY: MISC_FEATURE
<222> LOCATION: (5)..(5)
<223> OTHER INFORMATION: Beta3-E
<220> FEATURE:
<221> NAME/KEY: MISC_FEATURE
<222> LOCATION: (8)..(8)
<223> OTHER INFORMATION: Beta3-R
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: trans-2-aminocyclopentanecarboxylic acid
<220> FEATURE:
<221> NAME/KEY: MISC_FEATURE
<222> LOCATION: (19)..(19)
<223> OTHER INFORMATION: trans-2-aminocyclopentanecarboxylic acid
<220> FEATURE:
<221> NAME/KEY: MISC_FEATURE
<222> LOCATION: (22)..(22)
<223> OTHER INFORMATION: trans-3-aminopyrrolidine-4-carboxylic acid
<220> FEATURE:
<221> NAME/KEY: MISC_FEATURE
<222> LOCATION: (26)..(26)
<223> OTHER INFORMATION: trans-2-aminocyclopentanecarboxylic acid
<220> FEATURE:
<221> NAME/KEY: MISC_FEATURE
```

```
<222> LOCATION: (29)..(29)
<223> OTHER INFORMATION: trans-3-aminopyrrolidine-4-carboxylic acid
<220> FEATURE:
<221> NAME/KEY: MISC_FEATURE
<222> LOCATION: (33)..(33)
<223> OTHER INFORMATION: trans-2-aminocyclopentanecarboxylic acid
<220> FEATURE:
<221> NAME/KEY: MISC_FEATURE
<222> LOCATION: (36)..(36)
<223> OTHER INFORMATION: trans-3-aminopyrrolidine-4-carboxylic acid

<400> SEQUENCE: 29

Arg Thr Trp Glu Glu Trp Asp Arg Ala Ile Ala Glu Tyr Ala Xaa Arg
1               5                   10                  15

Ile Glu Xaa Leu Ile Glx Ala Ala Gln Xaa Gln Gln Glx Lys Asn Glu
            20                  25                  30

Xaa Ala Leu Glx Glu Leu
        35

<210> SEQ ID NO 30
<211> LENGTH: 38
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Beta3-R
<220> FEATURE:
<221> NAME/KEY: MISC_FEATURE
<222> LOCATION: (5)..(5)
<223> OTHER INFORMATION: Beta3-E
<220> FEATURE:
<221> NAME/KEY: MISC_FEATURE
<222> LOCATION: (8)..(8)
<223> OTHER INFORMATION: Beta3-R
<220> FEATURE:
<221> NAME/KEY: MISC_FEATURE
<222> LOCATION: (12)..(12)
<223> OTHER INFORMATION: Beta3-E
<220> FEATURE:
<221> NAME/KEY: MISC_FEATURE
<222> LOCATION: (15)..(15)
<223> OTHER INFORMATION: Beta3-R
<220> FEATURE:
<221> NAME/KEY: MISC_FEATURE
<222> LOCATION: (19)..(19)
<223> OTHER INFORMATION: Beta3-E
<220> FEATURE:
<221> NAME/KEY: MISC_FEATURE
<222> LOCATION: (22)..(22)
<223> OTHER INFORMATION: Beta3-R
<220> FEATURE:
<221> NAME/KEY: MISC_FEATURE
<222> LOCATION: (26)..(26)
<223> OTHER INFORMATION: Beta3-E
<220> FEATURE:
<221> NAME/KEY: MISC_FEATURE
<222> LOCATION: (29)..(29)
<223> OTHER INFORMATION: Beta3-R
<220> FEATURE:
<221> NAME/KEY: MISC_FEATURE
<222> LOCATION: (33)..(33)
<223> OTHER INFORMATION: Beta3-E
<220> FEATURE:
<221> NAME/KEY: MISC_FEATURE
<222> LOCATION: (36)..(36)
<223> OTHER INFORMATION: Beta3-R

<400> SEQUENCE: 30

Arg Thr Trp Glu Glu Trp Asp Arg Ala Ile Ala Glu Tyr Ala Arg Arg
1               5                   10                  15
```

```
Ile Glu Glu Leu Ile Arg Ala Ala Gln Glu Gln Gln Arg Lys Asn Glu
            20                  25                  30

Glu Ala Leu Arg Glu Leu
        35
```